(12) United States Patent  
Chassot et al.

(10) Patent No.: US 12,262,968 B2
(45) Date of Patent: Apr. 1, 2025

(54) TRANSLATIONAL INSTRUMENT INTERFACE FOR SURGICAL ROBOT AND SURGICAL ROBOT SYSTEMS COMPRISING THE SAME

(71) Applicant: Distalmotion SA, Epalinges (CH)

(72) Inventors: Julien Chassot, Lechelles (CH); Michael Friedrich, Bern (CH)

(73) Assignee: Distalmotion SA, Epalinges (CH)

( * ) Notice: Subject to any disclaimer, the term of this patent is extended or adjusted under 35 U.S.C. 154(b) by 536 days.

(21) Appl. No.: 17/372,163

(22) Filed: Jul. 9, 2021

(65) Prior Publication Data

US 2021/0330408 A1 Oct. 28, 2021

Related U.S. Application Data

(63) Continuation of application No. 15/976,812, filed on May 10, 2018, now Pat. No. 11,058,503.
(Continued)

(51) Int. Cl.
*A61B 17/00* (2006.01)
*A61B 34/00* (2016.01)
(Continued)

(52) U.S. Cl.
CPC ............. *A61B 34/37* (2016.02); *A61B 17/00* (2013.01); *A61B 34/71* (2016.02); *A61B 46/10* (2016.02);
(Continued)

(58) Field of Classification Search
CPC ......... A61B 34/35; A61B 34/37; A61B 34/71; A61B 2034/302; A61B 2034/305;
(Continued)

(56) References Cited

U.S. PATENT DOCUMENTS 2,764,301 A 9/1956 Goertz et al.
2,771,199 A 11/1956 Jelatis
(Continued)

FOREIGN PATENT DOCUMENTS

CN 101027010 A 8/2007
CN 101584594 A 11/2009
(Continued)

OTHER PUBLICATIONS

US 9,232,978 B2, 01/2016, Shellenberger et al. (withdrawn)
(Continued)

*Primary Examiner* — Michael J Lau
*Assistant Examiner* — Anh-Khoa N Dinh
(74) *Attorney, Agent, or Firm* — Cooley LLP

(57) ABSTRACT

Surgical instruments for use in a surgical robot are provided herein. The instruments are preferably part of a translational instrument interface and are removably coupled to the surgical robot. In one aspect, the translational instrument interface has a slave hub mounted on a distal end of the slave unit, a sterile shield insertable within the slave hub, and an instrument having an end-effector for contacting tissue insertable within the sterile shield. The instrument may be disposable after a single use. The handle of the surgical robot is preferably coupled to the translational instrument interface such that actuation at the handle causes movement of the end-effector for performing surgery.

19 Claims, 28 Drawing Sheets

Related U.S. Application Data

(60) Provisional application No. 62/505,018, filed on May 11, 2017.

(51) Int. Cl.
  *A61B 34/30* (2016.01)
  *A61B 34/37* (2016.01)
  *A61B 46/10* (2016.01)
  *A61B 90/94* (2016.01)
  *A61B 34/35* (2016.01)
  *A61B 90/00* (2016.01)
  *A61B 90/90* (2016.01)

(52) U.S. Cl.
  CPC ...... *A61B 90/94* (2016.02); *A61B 2017/0023* (2013.01); *A61B 2017/00398* (2013.01); *A61B 2017/00477* (2013.01); *A61B 2017/00539* (2013.01); *A61B 2034/302* (2016.02); *A61B 2034/305* (2016.02); *A61B 34/35* (2016.02); *A61B 2034/715* (2016.02); *A61B 2090/0812* (2016.02); *A61B 90/90* (2016.02); *A61B 2560/0238* (2013.01)

(58) Field of Classification Search
  CPC .............. A61B 2034/715; A61B 17/00; A61B 2017/0023; A61B 2017/00398; A61B 2017/00477; A61B 2017/00539; A61B 46/10; A61B 90/90; A61B 90/94; A61B 2090/0812; A61B 2560/0238; A61B 34/30; A61B 34/70
  USPC .......................................................... 606/1
  See application file for complete search history.

(56) References Cited

U.S. PATENT DOCUMENTS

| | | |
|---|---|---|
| 2,774,488 A | 12/1956 | Goertz et al. |
| 2,846,084 A | 8/1958 | Goertz et al. |
| 3,065,863 A | 11/1962 | Saunders, Jr. et al. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker et al. |
| 3,995,209 A | 11/1976 | Weston |
| 4,221,516 A | 9/1980 | Haaker et al. |
| 4,522,196 A | 6/1985 | Cunningham et al. |
| 4,557,164 A | 12/1985 | Krampe |
| 4,756,655 A | 7/1988 | Jameson |
| 4,838,797 A | 6/1989 | Dodier |
| 5,147,357 A | 9/1992 | Rose et al. |
| 5,176,352 A | 1/1993 | Braun |
| 5,207,114 A | 5/1993 | Salisbury, Jr. et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,591,119 A | 1/1997 | Adair |
| 5,599,151 A | 2/1997 | Daum et al. |
| 5,603,723 A | 2/1997 | Aranyi et al. |
| 5,631,973 A | 5/1997 | Green |
| 5,649,955 A | 7/1997 | Hashimoto et al. |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,779,727 A | 7/1998 | Orejola |
| 5,784,542 A | 7/1998 | Ohm et al. |
| 5,792,045 A | 8/1998 | Adair |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,855,583 A | 1/1999 | Wang et al. |
| 5,876,325 A | 3/1999 | Mizuno et al. |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,063,095 A | 5/2000 | Wang et al. |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,375,610 B2 | 4/2002 | Verschuur |
| 6,394,998 B1 | 5/2002 | Wallace et al. |
| 6,435,794 B1 | 8/2002 | Springer |
| 6,436,107 B1 | 8/2002 | Wang et al. |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,799,065 B1 | 9/2004 | Niemeyer |
| 6,817,974 B2 | 11/2004 | Cooper et al. |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,025,064 B2 | 4/2006 | Wang et al. |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,122,032 B2 | 10/2006 | Shinmura et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,331,967 B2 | 2/2008 | Lee et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,886,743 B2 | 2/2011 | Cooper et al. |
| 7,890,211 B2 | 2/2011 | Green |
| 7,914,521 B2 | 3/2011 | Wang et al. |

(56) References Cited

U.S. PATENT DOCUMENTS

| | | |
|---|---|---|
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,226,546 B2 | 7/2012 | Belson |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,303,576 B2 * | 11/2012 | Brock .................. A61B 34/74 606/1 |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,433,389 B2 | 4/2013 | Geiger et al. |
| 8,435,171 B2 | 5/2013 | Sholev |
| 8,496,152 B2 | 7/2013 | Viola |
| 8,500,132 B2 | 8/2013 | Norton |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,608,773 B2 | 12/2013 | Tierney et al. |
| 8,616,431 B2 | 12/2013 | Timm et al. |
| 8,617,203 B2 | 12/2013 | Stefanchik et al. |
| 8,644,988 B2 | 2/2014 | Prisco et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,753,346 B2 | 6/2014 | Suarez et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,888,688 B2 | 11/2014 | Julian et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,060,795 B2 | 6/2015 | Meenink |
| 9,084,606 B2 | 7/2015 | Greep |
| 9,089,351 B2 | 7/2015 | Park et al. |
| 9,113,860 B2 | 8/2015 | Viola et al. |
| 9,113,861 B2 | 8/2015 | Martin et al. |
| 9,119,657 B2 | 9/2015 | Shelton, IV et al. |
| 9,144,456 B2 | 9/2015 | Rosa et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,314,310 B2 | 4/2016 | Kirschenman et al. |
| 9,333,040 B2 | 5/2016 | Shellenberger et al. |
| 9,345,545 B2 | 5/2016 | Shellenberger et al. |
| 9,358,031 B2 | 6/2016 | Manzo |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,713,509 B2 | 7/2017 | Schuh et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| 9,883,915 B2 | 2/2018 | Rogers et al. |
| 9,884,427 B2 | 2/2018 | Low et al. |
| 9,895,142 B2 | 2/2018 | Sato et al. |
| D816,243 S | 4/2018 | Barber |
| 9,937,013 B2 | 4/2018 | Frimer et al. |
| 9,937,626 B2 | 4/2018 | Rockrohr |
| 9,943,372 B2 | 4/2018 | Sholev et al. |
| 9,943,377 B2 | 4/2018 | Yates et al. |
| 9,980,743 B2 | 5/2018 | Grace et al. |
| 9,993,313 B2 | 6/2018 | Schuh et al. |
| 10,028,792 B2 | 7/2018 | Frimer et al. |
| 10,039,609 B2 | 8/2018 | Frimer et al. |
| 10,039,820 B2 | 8/2018 | Coller et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,179,413 B2 | 1/2019 | Rockrohr |
| 10,201,392 B2 | 2/2019 | Frimer et al. |
| 10,265,129 B2 | 4/2019 | Beira |
| 10,299,873 B2 | 5/2019 | Hares et al. |
| 10,325,072 B2 | 6/2019 | Beira et al. |
| 10,357,320 B2 | 7/2019 | Beira |
| 10,357,324 B2 | 7/2019 | Flatt et al. |
| 10,363,055 B2 | 7/2019 | Beira et al. |
| 10,413,374 B2 | 9/2019 | Chassot et al. |
| 10,433,925 B2 | 10/2019 | Shelton, IV et al. |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 10,736,705 B2 | 8/2020 | Scheib et al. |
| 10,786,272 B2 | 9/2020 | Beira |
| 10,786,329 B2 | 9/2020 | Schuh et al. |
| 10,792,113 B2 | 10/2020 | Cuthbertson et al. |
| 10,813,713 B2 | 10/2020 | Koch, Jr. et al. |
| 10,864,049 B2 | 12/2020 | Beira |
| 10,864,052 B2 | 12/2020 | Beira |
| 11,039,820 B2 | 6/2021 | Beira |
| 11,058,503 B2 | 7/2021 | Chassot et al. |

(56) References Cited

U.S. PATENT DOCUMENTS

| | | |
|---|---|---|
| 11,076,922 B2 | 8/2021 | Beira et al. |
| 11,154,373 B2 | 10/2021 | Abbott et al. |
| 11,173,003 B2 | 11/2021 | Cassell et al. |
| 11,200,980 B2 | 12/2021 | Beira et al. |
| 11,207,143 B2* | 12/2021 | Abbott .................. B25J 9/123 |
| 11,234,782 B2 | 2/2022 | Devengenzo et al. |
| 11,278,364 B2 | 3/2022 | Cooper et al. |
| 11,291,442 B2 | 4/2022 | Wixey et al. |
| 11,324,619 B1 | 5/2022 | Yacoby et al. |
| 11,337,716 B2 | 5/2022 | Beira |
| 11,389,259 B2 | 7/2022 | Dachs, II |
| 11,399,886 B2 | 8/2022 | Kerver et al. |
| 11,426,187 B2 | 8/2022 | Brodbeck et al. |
| 11,432,893 B2 | 9/2022 | Itkowitz et al. |
| 11,478,315 B2 | 10/2022 | Beira |
| 11,490,977 B2 | 11/2022 | Schena et al. |
| 11,490,978 B2 | 11/2022 | Klein et al. |
| 11,510,745 B2 | 11/2022 | Chassot et al. |
| 11,547,506 B2 | 1/2023 | Devengenzo et al. |
| 11,564,760 B2 | 1/2023 | Steger et al. |
| 11,571,195 B2 | 2/2023 | Beira |
| 11,607,281 B2 | 3/2023 | Turner |
| 11,627,948 B2 | 4/2023 | Brisson et al. |
| 11,633,246 B2 | 4/2023 | Cavalier et al. |
| 11,633,249 B2 | 4/2023 | Smaby et al. |
| 11,648,076 B2 | 5/2023 | Bailey |
| 11,659,978 B2 | 5/2023 | Larkin et al. |
| 11,660,154 B2 | 5/2023 | Miller et al. |
| 11,672,621 B2 | 6/2023 | Hulford et al. |
| 11,766,303 B2 | 9/2023 | Devengenzo et al. |
| 11,793,585 B2 | 10/2023 | Cassell et al. |
| 11,806,016 B2 | 11/2023 | Ragosta et al. |
| 11,826,017 B2 | 11/2023 | Diolaiti et al. |
| 11,859,967 B2 | 1/2024 | Diolaiti |
| 11,911,069 B2 | 2/2024 | Lambrecht et al. |
| 11,934,594 B2 | 3/2024 | Diolaiti et al. |
| 11,944,337 B2 | 4/2024 | Beira |
| 11,960,665 B2 | 4/2024 | Bailey et al. |
| 11,969,889 B2 | 4/2024 | Cooper et al. |
| 11,974,826 B2 | 5/2024 | Steger et al. |
| 11,974,827 B2 | 5/2024 | Gomez et al. |
| 12,016,646 B2 | 6/2024 | Itkowitz et al. |
| 12,089,809 B2 | 9/2024 | Larkin et al. |
| 12,114,945 B2 | 10/2024 | Dupont et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll et al. |
| 2003/0013949 A1 | 1/2003 | Moll et al. |
| 2003/0155747 A1 | 8/2003 | Bridges |
| 2003/0208186 A1 | 11/2003 | Moreyra |
| 2003/0216715 A1 | 11/2003 | Moll et al. |
| 2004/0049205 A1 | 3/2004 | Lee et al. |
| 2004/0116906 A1 | 6/2004 | Lipow |
| 2004/0133189 A1 | 7/2004 | Sakurai |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0216045 A1 | 9/2005 | Young et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2009/0326322 A1 | 12/2009 | Diolaiti |
| 2009/0326552 A1 | 12/2009 | Diolaiti |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0234857 A1 | 9/2010 | Itkowitz et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0082462 A1 | 4/2011 | Suarez et al. |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0282491 A1 | 11/2011 | Prisco et al. |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1* | 7/2013 | Olson .................. A61B 34/30 606/130 |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304070 A1 | 11/2013 | Nelson et al. |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |

(56) References Cited

U.S. PATENT DOCUMENTS

| | | |
|---|---|---|
| 2014/0018960 A1 | 1/2014 | Itkowitz |
| 2014/0039527 A1 | 2/2014 | Avelar et al. |
| 2014/0052152 A1* | 2/2014 | Au .................. A61B 34/37 606/130 |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0277203 A1 | 9/2014 | Atoulikian et al. |
| 2014/0340796 A1 | 11/2014 | Sandhu et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1* | 6/2015 | Lohmeier .......... A61B 17/00 606/130 |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0302876 A1 | 10/2016 | Teichtmann |
| 2016/0303743 A1 | 10/2016 | Rockrohr |
| 2016/0346053 A1 | 12/2016 | Beira |
| 2016/0374766 A1 | 12/2016 | Schuh |
| 2017/0020615 A1* | 1/2017 | Koenig .................. A61B 34/72 |
| 2017/0065364 A1 | 3/2017 | Schuh et al. |
| 2017/0196599 A1 | 7/2017 | Kwon et al. |
| 2017/0215976 A1 | 8/2017 | Nowlin et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0168760 A1 | 6/2018 | Koch, Jr. et al. |
| 2018/0214223 A1 | 8/2018 | Turner |
| 2018/0242991 A1 | 8/2018 | Beira |
| 2018/0353251 A1 | 12/2018 | Cuthbertson et al. |
| 2018/0353252 A1 | 12/2018 | Chassot et al. |
| 2018/0360548 A1 | 12/2018 | Marshall et al. |
| 2019/0133698 A1 | 5/2019 | Beira et al. |
| 2019/0239968 A1 | 8/2019 | Beira |
| 2019/0328473 A1 | 10/2019 | Chassot et al. |
| 2020/0105412 A1 | 4/2020 | Beira |
| 2020/0268464 A1 | 8/2020 | Beira |
| 2021/0106348 A1 | 4/2021 | Beira |
| 2021/0330407 A1 | 10/2021 | Chassot et al. |
| 2021/0369360 A1 | 12/2021 | Beira et al. |
| 2022/0280179 A1 | 9/2022 | Beira |
| 2023/0054176 A1 | 2/2023 | Beira |
| 2023/0082915 A1 | 3/2023 | Chassot et al. |
| 2023/0125213 A1 | 4/2023 | Chassot et al. |
| 2023/0149002 A1 | 5/2023 | Beira |
| 2024/0000525 A1 | 1/2024 | Cassell et al. |
| 2024/0033026 A1 | 2/2024 | Chassot et al. |
| 2024/0197351 A1 | 6/2024 | Beira |
| 2024/0216087 A1 | 7/2024 | Dupont et al. |

FOREIGN PATENT DOCUMENTS

| | | |
|---|---|---|
| CN | 101637402 A | 2/2010 |
| CN | 101732093 A | 6/2010 |
| CN | 103717355 A | 4/2014 |
| DE | 4303311 A1 | 8/1994 |
| DE | 19652792 C2 | 5/1999 |
| DE | 10314827 B3 | 4/2004 |
| DE | 10314828 B3 | 7/2004 |
| DE | 102012008537 A1 | 10/2013 |
| DE | 102012222755 A1 | 6/2014 |
| DE | 102014205036 A1 | 9/2015 |
| DE | 102014205159 A1 | 9/2015 |
| EP | 0595291 A1 | 5/1994 |
| EP | 0621009 A1 | 10/1994 |
| EP | 0677275 A2 | 10/1995 |
| EP | 0776739 A2 | 6/1997 |
| EP | 1254642 A1 | 11/2002 |
| EP | 1279371 B1 | 12/2004 |
| EP | 1886630 A2 | 2/2008 |
| EP | 1889579 A2 | 2/2008 |
| EP | 1889583 A1 | 2/2008 |
| EP | 2058090 A2 | 5/2009 |
| EP | 1977677 B1 | 8/2009 |
| EP | 2095778 A1 | 9/2009 |
| EP | 1889583 B1 | 4/2011 |
| EP | 2377477 B1 | 5/2012 |
| EP | 2473119 A2 | 7/2012 |
| EP | 2305144 B1 | 10/2012 |
| EP | 2044893 B1 | 7/2013 |
| EP | 2653110 A1 | 10/2013 |
| EP | 2679192 A2 | 1/2014 |
| EP | 2736680 A2 | 6/2014 |
| EP | 2777561 A1 | 9/2014 |
| EP | 2783643 A1 | 10/2014 |
| EP | 2837340 A1 | 2/2015 |
| EP | 2837354 A1 | 2/2015 |
| EP | 2554131 B1 | 8/2015 |
| EP | 2777561 B1 | 10/2015 |
| EP | 2979657 A1 | 2/2016 |
| EP | 2837340 B1 | 10/2016 |
| EP | 3111879 A1 | 1/2017 |
| EP | 2783643 B1 | 1/2019 |
| EP | 3613377 A1 | 2/2020 |
| GB | 834244 A | 5/1960 |
| GB | 969899 A | 9/1964 |
| JP | 2004041580 A | 2/2004 |
| JP | 3653856 B2 | 6/2005 |
| JP | 2007290096 A | 11/2007 |
| JP | 2008104620 A | 5/2008 |
| JP | 2009018027 A | 1/2009 |
| KR | 20110032444 A | 3/2011 |
| KR | 20130031403 A | 3/2013 |
| SU | 722754 A1 | 3/1980 |
| WO | WO-8200611 A1 | 3/1982 |
| WO | WO-9743942 A1 | 11/1997 |
| WO | WO-9825666 A1 | 6/1998 |
| WO | WO-0197717 A1 | 12/2001 |
| WO | WO-03067341 A2 | 8/2003 |
| WO | WO-03086219 A2 | 10/2003 |
| WO | WO-2004052171 A2 | 6/2004 |

(56) References Cited

FOREIGN PATENT DOCUMENTS

| | | |
|---|---|---|
| WO | WO-2005009482 A2 | 2/2005 |
| WO | WO-2005046500 A1 | 5/2005 |
| WO | WO-2006086663 A2 | 8/2006 |
| WO | WO-2007133065 A1 | 11/2007 |
| WO | WO-2007146987 A2 | 12/2007 |
| WO | WO-2008070556 A1 | 6/2008 |
| WO | WO-2008130235 A2 | 10/2008 |
| WO | WO-2009091497 A2 | 7/2009 |
| WO | WO-2009095893 A2 | 8/2009 |
| WO | WO-2009145572 A2 | 12/2009 |
| WO | WO-2009157719 A2 | 12/2009 |
| WO | WO-2010019001 A2 | 2/2010 |
| WO | WO-2010030114 A2 | 3/2010 |
| WO | WO-2010050771 A2 | 5/2010 |
| WO | WO-2010083480 A2 | 7/2010 |
| WO | WO-2010096580 A1 | 8/2010 |
| WO | WO-2010130817 A1 | 11/2010 |
| WO | WO-2011025818 A1 | 3/2011 |
| WO | WO-2011027183 A2 | 3/2011 |
| WO | WO-2011108840 A2 | 9/2011 |
| WO | WO-2011123669 A1 | 10/2011 |
| WO | WO-2011161626 A1 | 12/2011 |
| WO | WO-2012020386 A1 | 2/2012 |
| WO | WO-2012049623 A1 | 4/2012 |
| WO | WO-2013007784 A1 | 1/2013 |
| WO | WO-2013014621 A2 | 1/2013 |
| WO | WO-2014012780 A1 | 1/2014 |
| WO | WO-2014018447 A1 | 1/2014 |
| WO | WO-2014067804 A1 | 5/2014 |
| WO | WO-2014094716 A1 | 6/2014 |
| WO | WO-2014094717 A1 | 6/2014 |
| WO | WO-2014094718 A1 | 6/2014 |
| WO | WO-2014094719 A1 | 6/2014 |
| WO | WO-2014139023 A1 | 9/2014 |
| WO | WO-2014145148 A2 | 9/2014 |
| WO | WO-2014156221 A1 | 10/2014 |
| WO | WO-2014201010 A1 | 12/2014 |
| WO | WO-2014201538 A1 | 12/2014 |
| WO | WO-2015081946 A1 | 6/2015 |
| WO | WO-2015081947 A1 | 6/2015 |
| WO | WO-2015088647 A1 | 6/2015 |
| WO | WO-2015088655 A1 | 6/2015 |
| WO | WO-2015111475 A1 | 7/2015 |
| WO | WO-2015113933 A1 | 8/2015 |
| WO | WO-2015129383 A1 | 9/2015 |
| WO | WO-2015139674 A1 | 9/2015 |
| WO | WO-2015175200 A1 | 11/2015 |
| WO | WO-2016030767 A1 | 3/2016 |
| WO | WO-2016083189 A1 | 6/2016 |
| WO | WO-2016097861 A1 | 6/2016 |
| WO | WO-2016097864 A2 | 6/2016 |
| WO | WO-2016097868 A1 | 6/2016 |
| WO | WO-2016097871 A1 | 6/2016 |
| WO | WO-2016097873 A2 | 6/2016 |
| WO | WO-2016154173 A1 | 9/2016 |
| WO | WO-2016162751 A1 | 10/2016 |
| WO | WO-2016162752 A1 | 10/2016 |
| WO | WO-2016183054 A1 | 11/2016 |
| WO | WO-2016189284 A1 | 12/2016 |
| WO | WO-2016209891 A1 | 12/2016 |
| WO | WO-2017015599 A1 | 1/2017 |
| WO | WO-2017037532 A1 | 3/2017 |
| WO | WO-2017064301 A1 | 4/2017 |
| WO | WO-2017064303 A1 | 4/2017 |
| WO | WO-2017064305 A1 | 4/2017 |
| WO | WO-2017064306 A1 | 4/2017 |
| WO | WO-2017134077 A1 | 8/2017 |
| WO | WO-2017220978 A1 | 12/2017 |
| WO | WO-2018142112 A1 | 8/2018 |
| WO | WO-2018162921 A1 | 9/2018 |
| WO | WO-2018207136 A1 | 11/2018 |
| WO | WO-2019099346 A2 | 5/2019 |
| WO | WO-2020131304 A1 | 6/2020 |
| WO | WO-2020141487 A2 | 7/2020 |
| WO | WO-2020237400 A1 | 12/2020 |
| WO | WO-2020263870 A1 | 12/2020 |
| WO | WO-2023037273 A1 | 3/2023 |
| WO | WO-2023073565 A1 | 5/2023 |
| WO | WO-2024084422 A1 | 4/2024 |

OTHER PUBLICATIONS

Abbott, et al., Design of an Endoluminal Notes Robotic System, IEEE/RSJ International Conference on Intelligent Robots and Systems, 2007, San Diego, CA (pp. 410-416).

Aesculap Surgical Technologies, Aesculap.RTM. Caiman.RTM., Advanced Bipolar Seal and Cut Technology Brochure, 6 pages (retrieved Aug. 31, 2015).

Arata, et al., Development of a dexterous minimally-invasive surgical system with augmented force feedback capability, IEEE/RSJ International Conference on Intelligent Robots and Systems, 2005 (pp. 3207-3212).

Cavusoglu, et al., Laparoscopic Telesurgical Workstation, IEEE Transactions on Robotics and Automation, (15)4:728-739 (1999).

Charles, et al., Dexterity-enhanced Telerobotic Microsurgery, 8th International Conference Advanced Robotics, pp. 5-10 (1997).

Dachs, et al., Novel Surgical Robot Design: Minimizing the Operating Envelope With in the Sterile Field, 28th International Conference, IEEE Engineering in Medicine Biology Society, 2006, New York (pp. 1505-1508).

Dario, et al., "Novel Mechatronic Tool for Computer-Assisted Arthroscopy," IEEE Transactions on Information Technology in Biomedicine, 4(1):15-29 (Mar. 2000).

Extended European Search Report dated Mar. 18, 2020 in EP Patent Appl. Serial No. 19213231.4 (1031).

Focacci, et al., Lightweight Hand-held Robot for Laparoscopic Surgery, IEEE International Conference on Robotics & Automation, Rome, Italy, pp. 599-604 (2007).

Guthart, et al., The Intuitive. TM. Telesurgery System: Overview and Application, IEEE International Conference on Robotics & Automation, San Francisco, CA, 2000 (pp. 618-621).

Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).

Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).

International Search Report & Written Opinion dated Feb. 2, 2017 in Int'l PCT Patent Appl. Serial No. PCT/IB2016/001286.

International Search Report & Written Opinion dated Jan. 18, 2013 in Int'l PCT Patent Appl Serial No. PCT/IB2012/053786.

International Search Report & Written Opinion dated Jul. 10, 2018 in Int'l PCT Patent Appl. Serial No. PCT/IB2018/053272.

International Search Report & Written Opinion dated Jun. 10, 2016 in Int'l PCT Patent Appl Serial No. PCT/IB2015/002533.

International Search Report & Written Opinion dated Jun. 13, 2016 in Int'l PCT Patent Appl Serial No. PCT/IB2015/002493.

International Search Report & Written Opinion dated Mar. 30, 2015 in Int'l PCT Patent Appl Serial No. PCT/EP2015/051473.

International Search Report & Written Opinion dated May 23, 2016 in Int'l PCT Patent Appl Serial No. PCT/IB2015/002524.

International Search Report & Written Opinion dated May 24, 2016 in Int'l PCT Patent Appl Serial No. PCT/IB2015/002487.

International Search Report & Written Opinion dated Sep. 2, 2016 in Int'l PCT Patent Appl Serial No. PCT/IB2016/000543.

International Search Report & Written Opinion dated Feb. 17, 2016 in Int'l PCT Patent Appl. Serial No. PCT/IB2015/002095.

International Search Report & Written Opinion dated Mar. 23, 2012 in Int'l PCT Patent Appl. Serial No. PCT/IB2011/054476.

International Search Report & Written Opinion dated Apr. 26, 2016 in Int'l PCT Patent Appl. Serial No. PCT/IB2015/002512.

International Search Report & Written Opinion dated Jul. 7, 2020 in Int'l. PCT Patent Appl. Serial No. PCTIB2020050039.

International Search Report & Written Opinion dated Jul. 23, 2019 in Int'l PCT Patent Appl. No. PCT/IB2019/050961.

(56) References Cited

OTHER PUBLICATIONS

International Search Report & Written Opinion dated Aug. 25, 2016 in Int'l PCT Patent Appl. Serial No. PCT/IB2016/000542.
Ishii, et al., Development of a New Bending Mechanism and Its Application to Robotic Forceps Manipulator, IEEE International Conference on Robotics & Automation, Rome, Italy, 2007 (pp. 238-243).
Kobayashi, et al., Small Occupancy Robotic Mechanisms for Endoscopic Surgery, International Conference on Medical Image Computing and Computer assisted Interventions, 2002, (pp. 75-82).
Lang, et al., Intra-operative robotics: NeuroArm., Acta Neurochir Suppl, 109:231-236 (2011).
Mayer, et al., The Endo[PA]R System for Minimally Invasive Robotic Surgery, IEEE/RSJ International Conference on Intelligent Robots and Systems, Sendai, Japan, 2004 (pp. 3637-3642).
Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).
Mitsuishi, et al., Master-Slave Robotic Platform and its Feasibility Study for Micro-Neurosurgery, Int. J. Med. Robot., 9(2):180-9 (2013).
Morita, et al., Microsurgical Robotic System for the Deep Surgical Field: development of a Prototype and Feasibility Studies in Animal and Cadaveric Models, J. Neurosurg., 103(2):320-7 (2005).
Nakamura, et al., Multi-DOF Forceps Manipulator System for Laparoscopic Surgery-Mechanism miniaturized & Evaluation of New Interface, 4th International Conference on Medical Image Computing and Computer assisted Interventions (MICCAI2001), 2001 (pp. 606-613).
Peirs, et al., "Design of an Advanced Tool Guiding System for Robotic Surgery," IEEE International Conference on Robotics & Automation, Taipei, Taiwan, 2003, (pp. 2651-2656).
Salle, et al., Optimal Design of High Dexterity Modular MIS Instrument for Coronary Artery Bypass Grafting, IEEE International Conference on Robotics & Automation, New Orleans, LA, 2004, (pp. 1276-1281).
Seibold, et al., Prototype of Instrument for Minimally Invasive Surgery with 6-Axis Force Sensing Capability, IEEE International Conference on Robotics & Automation, Barcelona, Spain, 2005, (pp. 496-501).
Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).
Stryker(TM), Endoscopy, Take a Look Around, Ideal Eyes.TM. FFD122 Hd, Articulating Laparoscope Brochure, 2 pages (2009).
Swiss Search Report dated Jun. 4, 2012 in Swiss Patent Application No. CH 00702/12.
Tavakoli, et al., Force Reflective Master-Slave System for Minimally Invasive Surgery, IEEE/RSJ International Conference on Intelligent Robots and Systems, Las Vegas, NV, 2003, (pp. 3077-3082).
Taylor, et al., Steady-Hand Robotic System for Microsurgical Augmentation, The International Journal of Robotics Research, 18(12):1201-1210 (1999).
www.cttc.co/technologies/maestro-non-robotic-dexterous-laproscopic-instrum-ent-writs-providing-seven-degrees, Maestro: Non-Robotic Dexterous Laproscopic Instrument With a Wrist Providing Seven Degrees of Freedom, accessed Nov. 12, 2015, 4 pages.
Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).
Zeus, Robotic Surgical System, available at http://allaboutroboticsurgery.com/zeusrobot.html.
U.S. Appl. No. 13/878,924 / U.S. Pat. No. 10,092,359, filed May 17, 2013 / Oct. 9, 2018.
U.S. Appl. No. 14/233,184 / U.S. Pat. No. 9,696,700, filed Jan. 16, 2014 / Jul. 4, 2017.
U.S. Appl. No. 15/116,509 / U.S. Pat. No. 10,265,129, filed Aug. 3, 2016 / Apr. 23, 2019.
U.S. Appl. No. 15/506,659 / U.S. Pat. No. 10,357,320, filed Feb. 24, 2017 / Jul. 23, 2019.
U.S. Appl. No. 15/536,539 / U.S. Pat. No. 10,864,049, filed Jun. 15, 2017 / Dec. 15, 2020.
U.S. Appl. No. 15/536,562 / U.S. Pat. No. 10,864,052, filed Jun. 15, 2017 / Dec. 15, 2020.
U.S. Appl. No. 15/536,568 / U.S. Pat. No. 10,548,680, filed Jun. 15, 2017 / Feb. 4, 2020.
U.S. Appl. No. 15/536,573 / U.S. Pat. No. 11,039,820, filed Jun. 15, 2017 / Jun. 22, 2021.
U.S. Appl. No. 15/536,576 / U.S. Pat. No. 10,646,294, filed Jun. 15, 2017 / May 12, 2020.
U.S. Appl. No. 15/564,193 / U.S. Pat. No. 10,568,709, filed Oct. 3, 2017 / Feb. 25, 2020.
U.S. Appl. No. 15/564,194 / U.S. Pat. No. 10,363,055, filed Oct. 3, 2017 / Jul. 30, 2019.
U.S. Appl. No. 15/633,611 / U.S. Pat. No. 10,325,072 ,filed Jun. 26, 2017 / Jun. 18, 2019.
U.S. Appl. No. 15/756,037 / U.S. Pat. No. 10,786,272, filed Feb. 27, 2018 / Sep. 29, 2020.
U.S. Appl. No. 15/976,812 / U.S. Pat. No. 11,058,503, filed May 10, 2018 / Jul. 13, 2021.
U.S. Appl. No. 16/153,695, filed Oct. 5, 2018.
U.S. Appl. No. 16/269,383 / U.S. Pat. No. 10,413,374, filed Feb. 6, 2019 / Sep. 17, 2019.
U.S. Appl. No. 16/389,854, filed Apr. 19, 2019.
U.S. Appl. No. 16/442,435 / U.S. Pat. No. 10,510,447, filed Jun. 14, 2019 / Dec. 17, 2019.
U.S. Appl. No. 16/505,585, filed Jul. 8, 2019.
U.S. Appl. No. 16/701,063, filed Dec. 2, 2019.
U.S. Appl. No. 16/870,870, filed May 8, 2020.
U.S. Appl. No. 17/032,631, filed Sep. 25, 2020.
U.S. Appl. No. 17/351,118, filed Jun. 17, 2021.
U.S. Appl. No. 17/364,246, filed Jun. 30, 2021.
Non-Final Office Action for U.S. Appl. No. 18/482,695 dated Dec. 28, 2023, 13 pages.
Notice of Allowance for U.S. Appl. No. 18/482,695 mailed Aug. 14, 2024, 9 pages.

* cited by examiner

TRANSLATIONAL INSTRUMENT INTERFACE FOR SURGICAL ROBOT AND SURGICAL ROBOT SYSTEMS COMPRISING THE SAME

CROSS-REFERENCE TO RELATED APPLICATION

This application is a continuation of U.S. patent application Ser. No. 15/976,812, filed May 10, 2018, now U.S. Pat. No. 11,058,503, which claims priority to U.S. Provisional Application Ser. No. 62/505,018, filed May 11, 2017, the entire contents of each of which are incorporated herein by reference.

FIELD OF USE

This application generally relates to remotely actuated surgical robots and disposable instruments for the same.

BACKGROUND

Numerous environments and applications call for remote actuation with teleoperated surgical devices. These applications include fine manipulation in assembly tasks, manipulation in narrow places, manipulation in dangerous or contaminated environments, manipulation in clean-room or sterile environments and manipulation in surgical environments, whether open field or minimally invasive. While these applications vary along parameters such as precise tolerances and typical end user, each demands many of the same features from a teleoperated system, such as the ability to carry out dexterous manipulation with high stiffness and precision along with force feedback.

Surgical applications are now discussed in more detail as a representative example of an application for a teleoperated device system where known devices exist but significant shortcomings are evident in the current state of the art.

Open surgery is still the standard technique for most surgical procedures. It has been used by the medical community for several decades and consists of performing the surgical tasks by making a long incision in the abdomen or other area of the body, through which traditional surgical tools are inserted. However, due to the long incision, this approach is extremely invasive for patients, resulting in substantial blood loss during surgery and, typically, long and painful recovery periods in a hospital setting.

In order to reduce the invasiveness of open surgery, laparoscopy, a minimally invasive technique, was developed. Instead of a single long incision, several small incisions are made in the patient through which long and thin surgical instruments and endoscopic cameras are inserted. Because of the minimally invasive nature of the procedure, this technique reduces blood loss and pain and shortens hospital stays. When performed by experienced surgeons, this technique can attain clinical outcomes similar to open surgery. However, despite the above-mentioned advantages, laparoscopy requires extremely advanced surgical skill to manipulate the rigid and long instrumentation. The entry incision acts as a point of rotation, decreasing the freedom for positioning and orientating the instruments inside the patient. The movements of the surgeon's hand about this incision are inverted and scaled-up relative to the instrument tip ("fulcrum effect"), which reduces dexterity and sensitivity and magnifies the tremors of the surgeon hands. In addition, the long and straight instruments force the surgeon to work in an uncomfortable posture for hands, arms and body, which can be tremendously tiring during several hours of an operation. Therefore, due to these drawbacks of laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of remote laparoscopy where the surgeon sits at a console manipulating two master manipulators to perform the operation through several small incisions. Like laparoscopy, the robotic approach is also minimally invasive, bringing the above-mentioned advantages over open surgery in terms of pain, blood loss, and recovery time. In addition, it also offers better ergonomy for the surgeon compared to open and laparoscopic techniques. However, although being technically easier, robotic surgery brings several negative aspects. A major disadvantage of these systems relates to the extremely high complexity of the existing robotic devices, which have complex mechatronic systems, leading to huge costs of acquisition and maintenance, which are not affordable for the majority of surgical departments worldwide. Another drawback of these systems comes from the fact that current surgical robots are large, competing for precious space within the operating room environment and significantly increasing preparation time. Access to the patient is thus impaired, which, together with a general lack of force-feedback, raises safety concerns. Yet another potential drawback of robotic systems is that any computer error could lead to undesirable drifting or movement of the surgical end-effector tool at or within the patient. Such computer errors would be especially problematic with macro movements of an end-effector in any of the three translational degrees-of-freedoms, i.e., left/right, upward/downward, inward/outward, which could result in catastrophic damage when the end-effector is positioned at or within a patient during surgery.

WO97/43942 to Madhani, WO98/25666 to Cooper, and U.S. Patent Application Publication No. 2010/0011900 to Burbank disclose a robotic teleoperated surgical instrument designed to replicate a surgeon's hand movements inside the patient's body. By means of a computerized, robotic interface, the instrument enables the performance of remote laparoscopy, wherein the surgeon sits at a console manipulating two joysticks to perform the operation through several small incisions. However, this system does not have autonomy or artificial intelligence, being essentially a sophisticated tool fully controlled by the surgeon. The control commands are transmitted between the robotic master and robotic slave by a complex computer-controlled mechatronic system, which is extremely costly to produce and maintain and difficult to use for the hospital staff.

WO2013/014621 to Beira, the entire contents of which are incorporated herein by reference, describes a mechanical teleoperated device for remote manipulation which comprises master-slave configuration including a slave unit driven by a kinematically equivalent master unit such that each part of the slave unit mimics the movement of each corresponding part of the master unit. Although the mechanical transmission system is well adapted to the device, the low-friction routing of the cables from handles through the entire kinematic chain to the instruments is costly, complex, and requires precise calibration and careful handling and maintenance.

In addition, current teleoperated surgical instruments utilize rotational coupling or a combination of rotational and translational coupling of the individual degrees-of-freedom between the drive unit and the surgical instrument. For example, U.S. Patent Application Publication No. 2016/0151115 to Karguth describes a coupling mechanism with translationary elements aimed at translational tip movements, and rotary elements for rotational instrument tip movements. In addition, WO2016/189284 to Hares describes a driving mechanism with a combined translational and rotational engagement, and U.S. Patent Application Publication No. 2002/0072736 to Tierney describes an interface with rotational coupling of the drivable degrees-of-freedom.

Because of the high manufacturing costs of robotic teleoperated surgical instruments and complex mechanical teleoperated surgical instruments utilizing rotational coupling of degrees-of-freedom, such instruments must be reused across multiple surgeries, adding complex reliability, reprocessing and performance requirements.

Accordingly, it would be desirable to provide a teleoperated device with a simple interchangeable distal instrument. It would further be desirable to have the instruments designed for use in a surgical environment such that the interchangeable distal instruments would be surgical instruments.

SUMMARY

The present invention overcomes the drawbacks of previously-known systems by providing surgical instruments to be removably coupled to a surgical robot. Advantageously, relatively low-cost surgical instruments that contact tissue during surgery are removable and may be disposable while the more complex, expensive components of the surgical robot are reusable. The surgical robot preferably includes one or two teleoperated surgical arms, each removably coupled to the surgical instrument via an interface, e.g., sterile shield. In this manner, sterility is maintained throughout a surgical procedure.

The handle(s) of the surgical robot is(are) mechanically and/or electrically coupled to the translational instrument interface. In a preferred embodiment, the translational instrument interface includes a slave hub having a plurality of drive units, the slave hub mounted on a distal end of the slave unit, a sterile shield insertable within the slave hub, and the surgical instrument which has an end-effector and is insertable within the sterile shield. The sterile shield may be disposable after a single use and may be pre-sterilized. Actuation at the handle(s) actuates movement of the end-effector of the surgical instrument in one or more degrees-of-freedom.

In accordance with one aspect, the instrument includes an elongated shaft having a proximal region, a distal region, and a lumen extending therebetween. The instrument has an end-effector having one or more degrees-of-freedom disposed in the distal region, and an actuator disposed in the proximal region. The actuator may be coupled to the end-effector via a plurality of force transmitting elements, e.g. cables and pulleys, or rod-based force transmission chains, disposed in the lumen and configured to be releasably engaged with the sterile shield of the surgical robot and to move the end-effector responsive to translational movement at the actuator. The instrument may be disposable after a single use, and may be pre-sterilized. The instrument may also include an instrument head disposed in the proximal region having a rotatable portion and a locking pin. The rotatable portion and locking pin allows the instrument to engage the sterile shield. The instrument head may also include a key that axially aligns the instrument with the sterile shield. The instrument further may include at least one tension cable coupled to the actuator such that the at least one tension cable provides a tension on the plurality of force transmitting elements.

In accordance with one aspect, the actuator includes a pair of engagers sized and shaped to be releasably coupled to a respective receptacle of a slave hub such that movement of one of the plurality of drive units induces translational movement at a first engager of the pair of engagers in a first direction and corresponding translational movement at a second engager of the pair of engagers in an opposite direction to thereby move the end-effector in a first degree-of-freedom of the plurality of degrees-of-freedom. Each pair of engagers preferably moves parallel to a longitudinal axis of the elongated shaft along a pathway at the proximal region responsive to translational movement at the sterile shield of the surgical robot. The actuator further may include second and third pairs of engagers, each independently movable responsive to translational movement at the sterile shield of the surgical robot to actuate movement in second and third degrees-of-freedom, respectively. The first, second, and third pairs of engagers are preferably coupled to the end effector via first, second, and third force transmitting elements, respectively. In this manner, translational movement at each pair of engagers actuates movement of the end-effector in a degree-of-freedom. In one embodiment, each pair of engagers includes a pair of hooks configured to engage corresponding receptacles at the sterile shield to the surgical robot.

A slave hub also is provided herein that is mounted to the slave unit of a teleoperated surgical arm. In accordance with one aspect, the slave hub has an opening sized and shaped to receive the sterile shield and the elongated shaft of the instrument. The sterile shield provides a sterile barrier between the surgical instrument and the slave hub as well as the teleoperated surgical arm. Accordingly, the sterile shield may include a proximal component configured to be received through the opening of the slave hub, and a distal component configured to be engaged with the proximal component when the proximal component is disposed within the opening of the slave hub. Either the proximal component or the distal component may have an asymmetric shape that orients the proximal component or the distal component relative to the opening in the slave hub. The slave hub may be rotated about an axis of the slave unit, such that the end-effector also rotates about the axis.

In accordance with an aspect, the slave hub includes a receptacle that releasably interengages with the actuator, wherein translational motion of the receptacle and actuator, when interengaged, actuates the end-effector via the force transmitting element. The slave hub further may include at least one tension cable coupled to the receptacle such that the at least one tension cable provides a tension on the receptacle when no instrument is plugged in. The drive units may be, e.g., an electric motor, a hydraulic element or other mechanical means, operatively coupled to the receptacle to cause translation of the receptacle and actuator. For example, rotary movement of the electric motor may induce translational movement at the actuator via a system of cables and pulleys, or a system of gears, leadscrews, and leadscrew nuts. Accordingly, the sterile shield includes a slide element that is coupled between the actuator and the receptacle. Preferably, the slide element automatically aligns the receptacle with the actuator.

In accordance with an aspect, the slave hub includes a receptacle that releasably interengages with the actuator, wherein translational motion of the receptacle and actuator, when interengaged, actuates the end-effector via the force transmitting element. The slave hub further may include at least one tension cable coupled to the receptacle such that the at least one tension cable provides a tension on the receptacle when no instrument is plugged in. The drive units may be, e.g., an electric motor, an hydraulic element or other mechanical means, operatively coupled to the receptacle to cause translation of the receptacle and actuator. For example, rotary movement of the electric motor may induce translational movement at the actuator via a system of cables and pulleys, or a system of gears, leadscrews, and leadscrew nuts. Accordingly, the sterile shield includes a slide element that is coupled between the actuator and the receptacle. Preferably, the slide element automatically aligns the receptacle with the actuator.

The teleoperated surgical instrument may include a control system coupled to the plurality of drive units. Additionally, the instrument may include an identification tag such that the control system detects information about the instrument from the identification tag. For example, the identification tag may encode one of an instrument type, serial number, calibration data, range-of-motion data, end-effector kinematics, or controlling offsets. The control system may also be coupled to a sensor that may sense misalignment of the instrument. Accordingly, the control system may generate an alert responsive to the sensor sensing misalignment of the instrument.

In accordance with one aspect of the present invention, the translational instrument interface which includes the surgical instrument having an end-effector is configured to be removably coupled to a teleoperated surgical instrument that may be purely mechanical, purely electromechanical, or a combination of mechanical and electromechanical. In one example, micro movements at the end-effector of the surgical instrument are actuated in three degrees-of-freedom, e.g., open/close, pitch, yaw, electromechanically while the macro movements in the three translational degrees-of-freedom of the end effector, i.e., left/right, upward/downward, inward/outward, are controlled mechanically by the teleoperated surgical instrument. The seventh degree-of-freedom, pronosupination, may be controlled electromechanically or mechanically in the example. Preferably, the surgical instrument is designed to be removably coupled to a slave unit of the teleoperated surgical instrument. In one embodiment, the teleoperated surgical instrument includes a master unit having force transmitting elements, e.g., a plurality of rigid master links and/or cables and pulleys, and master joints and a handle, and a slave unit having force transmitting elements, e.g., a plurality of rigid slave links and/or cables and pulleys, and slave joints. The master unit may be kinematically connected to the slave unit via the plurality of force transmission elements of both the master unit and the slave unit such that a movement of the master unit will be reproduced at the slave unit and each rigid link of the master unit remains parallel to a corresponding rigid link of the slave unit during such movement.

DETAILED DESCRIPTION

Figure 1A:
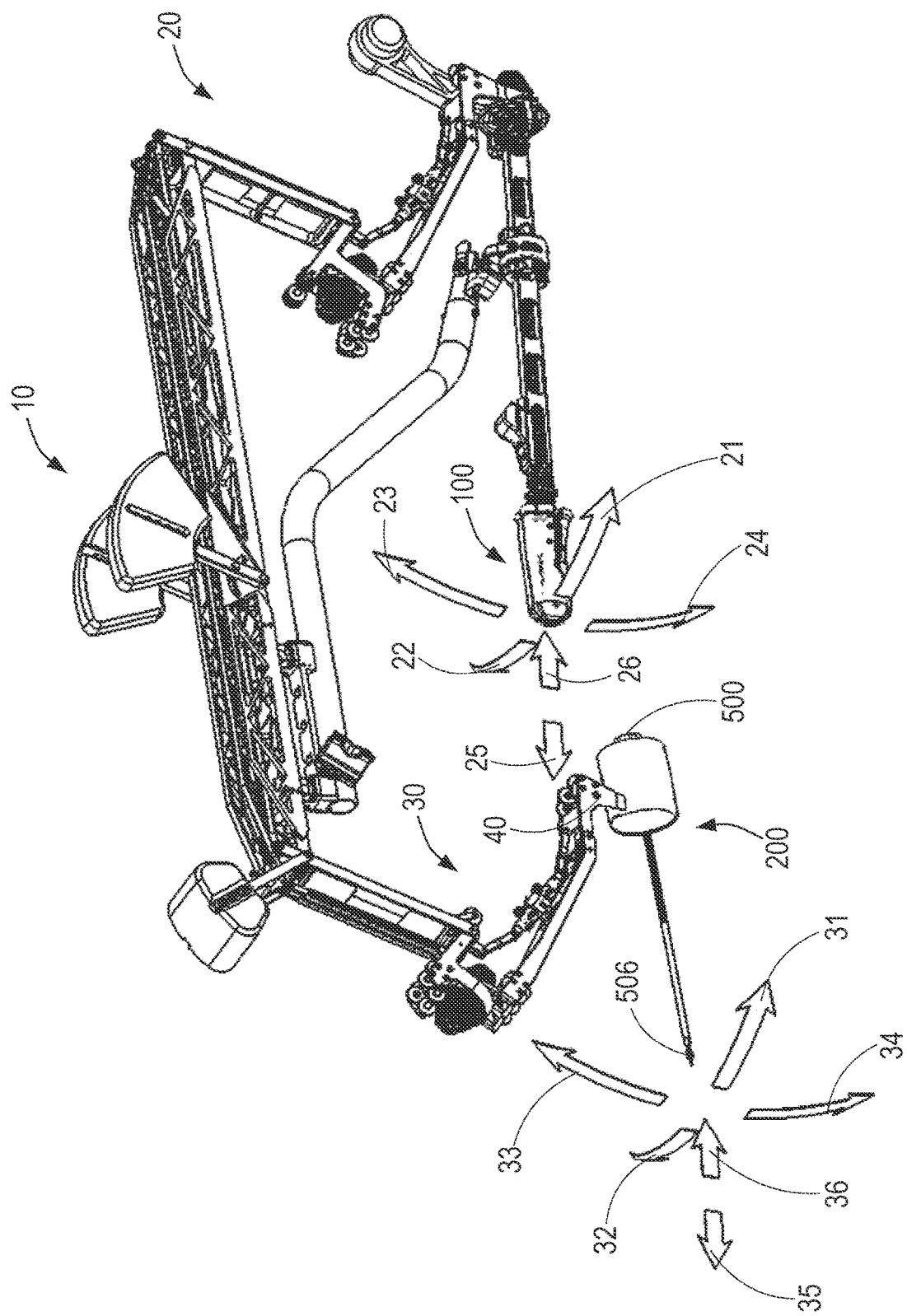
FIG. 1A shows an exemplary teleoperated surgical robot constructed in accordance with the principles of the present invention.

A teleoperated surgical instrument, which may be used in minimally invasive surgical procedures or in other applications, constructed in accordance with the principles of the present invention, is described herein. Referring to FIG. 1A, exemplary teleoperated surgical instrument 10 is illustrated having translational instrument interface 200 that includes detachable surgical instrument 500 having end-effector 506. Teleoperated surgical instrument 10 is designed in a master-slave configuration where slave unit 30, made of a plurality of rigid slave links and slave joints, is driven kinematically by master unit 20, made of a plurality of rigid master links and master joints. Preferably, each part of slave unit 30 mimics the movement of each corresponding part of master unit 20 without deviating, during operation of the device, from a remote-center-of-motion (RCM). As will be understood by one skilled in the art, two identical teleoperated surgical instruments may be operated simultaneously and independently from the other, e.g., one for the surgeon's left hand, and another one for the surgeon's right hand. Preferably, the teleoperated instrument is optimized for use in surgical procedures.

As shown in FIG. 1A, slave unit 30 has a plurality of slave joints and a plurality of force transmitting slave elements, e.g., rigid links, cables and pulleys, and/or rod-based force transmission chains, and master unit 20 has a plurality of master joints and a plurality of force transmitting master elements, e.g., rigid links, cables and pulleys, and/or rod-based force transmission chains. The slave joints of slave unit 30 and the master joints of master unit 20 may be coupled via the plurality of force transmitting master and slave elements extending between the plurality of master joints of master unit 20 and the plurality of slave joints of slave unit 30 such that a force of master unit 20 is reproduced by slave unit 30. For example, movement of master unit 20 via handle 100 may control positioning of distal end 40 of slave unit 30 and translational movement of surgical instrument 500 in the patient. In one embodiment, rigid links are used to translate movement in the three translational degrees-of-freedom such that each rigid link of master unit 20 remains parallel to a corresponding rigid link of slave unit 30 during such movement. An exemplary master-slave configuration of FIG. 1A is conceptually described in WO2016/162752 to Beira, the entire contents of which are incorporated herein by reference.

As seen in FIG. 1A, teleoperated surgical instrument 10 includes handle 100 and translational instrument interface 200. Handle 100 preferably includes a plurality of rigid handle links and handle joints kinematically connected to slave unit 30 via a plurality of force transmitting elements, e.g. rigid links, cables and pulleys, and/or rod-based force transmission chains, extending between the handle joints of handle 100 and the slave joints of slave unit 30 such that movement of handle 100 is reproduced by translational instrument interface 200. For example, movement of handle 100 may cause movement of end-effector 506 of translational instrument interface 200 in three translation degrees-of-freedom, e.g., left/right, upward/downward, inward/outward, as a force applied to a rigid link of handle 100 applies a force on the plurality of rigid links of master unit 30, which applies a force on the plurality of rigid links of slave unit 20, and which applies a force on end-effector 506. As shown in FIG. 1A, movement of handle 100 in left direction 21 causes end-effector 506 of translational instrument interface 200 to move in left direction 31, and movement of handle 100 in right direction 22 causes end-effector 506 of translational instrument interface 200 to move in right direction 32. Movement of handle 100 in upward direction 23 causes end-effector 506 of translational instrument interface 200 to move in upward direction 33, and movement of handle 100 in downward direction 24 causes end-effector 506 of translational instrument interface 200 to move in downward direction 34. Movement of handle 100 in outward direction 25 causes end-effector 506 of translational instrument interface 200 to move in outward direction 35, and movement of handle 100 in inward direction 26 causes end-effector 506 of translational instrument interface 200 to move in inward direction 36. In addition, handle 100 may be rotated causing pronosupination of instrument 500, e.g., rotation of instrument 500 about a longitudinal axis of instrument 500.

Handle 100 may be electrically coupled to translational instrument interface 200 and include a user interface, e.g., a plurality of sensors, haptic elements, buttons, switches, triggers, or the like, that when actuated, actuate movement of end-effector 506 of translational instrument interface 200 in a first articulation degree-of-freedom, e.g., pitch, and a second articulation degree-of-freedom, e.g., yaw, to provide a human wrist-like dexterity, and a third actuation degree-of-freedom, e.g., open or close. For example, handle 100 may be coupled to translational instrument interface 200 via electrical wires extending from handle 100, through master unit 20 and slave unit 30, to translational instrument interface 200.

Advantageously, teleoperated surgical instrument 10 may be designed such that micro movements at the end-effector in three degrees-of-freedom, e.g., open/close, pitch, yaw, are actuated electromechanically while the three translational degrees-of-freedom of the end effector, i.e., left/right, upward/downward, inward/outward, are controlled mechanically, via, for example, a plurality of rigid links. The seventh degree-of-freedom, pronosupination, may be controlled electromechanically or mechanically in the example. In this manner, teleoperated surgical instrument 10 provides the advantages of electromechanically controlled micro movements and the advantages of mechanically controlled macro movements.

Figure 1B:
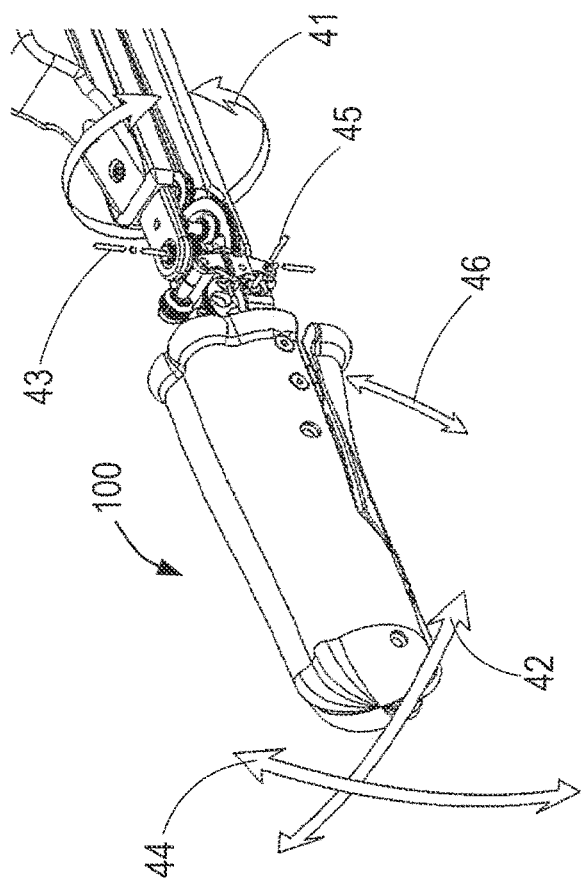
FIG. 1B illustrates four degrees-of-freedom of the end-effector controllable by the handle of FIG. 1A.
Figure 1B:
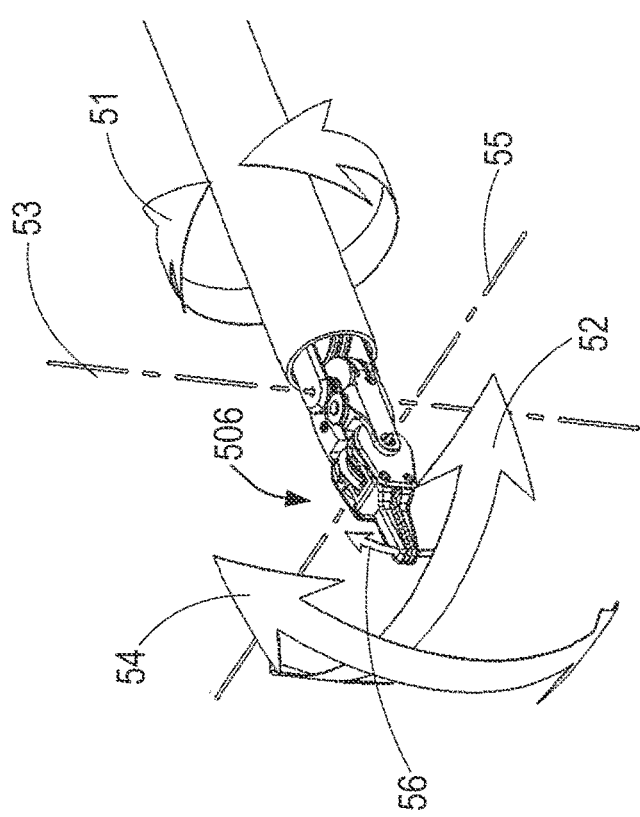

As shown in FIG. 1B, movement of handle 100 along direction 42 about axis 43 causes end-effector 506 of translational instrument interface 200 to yaw along direction 52 about axis 53. Movement of handle 100 along direction 44 about axis 45 causes end-effector 506 of translational instrument interface 200 to pitch along direction 54 about axis 55. Actuation of handle 100, e.g., pulling a trigger of handle 100 in direction 46, causes end-effector 506 of translational instrument interface 200 to open or close along direction 56. In one embodiment, handle 100 may have an interface, that when actuated, e.g., along axial direction 41, actuates movement of end-effector 506 of translational instrument interface 200 in a fourth rotation degree-of-freedom, e.g., pronosupination, along axial direction 51. The interface may include, for example, buttons, switches, triggers, or the like.

Translational instrument interface 200 may operate with other teleoperated surgical instruments, e.g., electromechanical and/or mechanical, as will be readily understood by one ordinarily skilled in the art. In addition, as described in further detail below, translational instrument interface 200 may be electromechanical, e.g., actuated via an electric motor, or mechanical, e.g., actuated via translational rigid link-driven transmission, hydraulic cylinders, and/or pneumatic elements. For example, when translational instrument interface 200 is electromechanical, translational instrument interface 200 may be attached to and operated by a mechanical teleoperated surgical instrument, e.g., teleoperated surgical instrument 10, such that the translation degrees-of-freedom, e.g., left/right, upward/downward, inward/outward, are actuated mechanically, whereas the articulation degrees-of-freedom, e.g., pitch and yaw, and the actuation degree-of-freedom, e.g., open/close, are actuated electromechanically. As another example, when translational instrument interface 200 is mechanical e.g., actuated via translational rigid link-driven transmission, hydraulic cylinders, or pneumatic elements, the translation degrees-of-freedom, e.g., left/right, upward/downward, inward/outward, are actuated mechanically and the articulation degrees-of-freedom, e.g., pitch and yaw, as well as the actuation degree-of-freedom, e.g., open/close, are actuated mechanically. Additionally, the rotation degree-of-freedom, e.g., pronosupination, may be actuated either electromechanically or mechanically via one or more cables and pulleys extending between handle 100 and translational instrument interface 200. Accordingly, in various examples, teleoperated surgical instrument 10 with translational instrument interface 200 has (i) seven degrees-of-freedom actuated mechanically, (ii) four degrees-of-freedom actuated mechanically and three degrees-of-freedom actuated electromechanically, or (iii) three degrees-of-freedom actuated mechanically and four degrees-of-freedom actuated electromechanically.

Figure 1C:
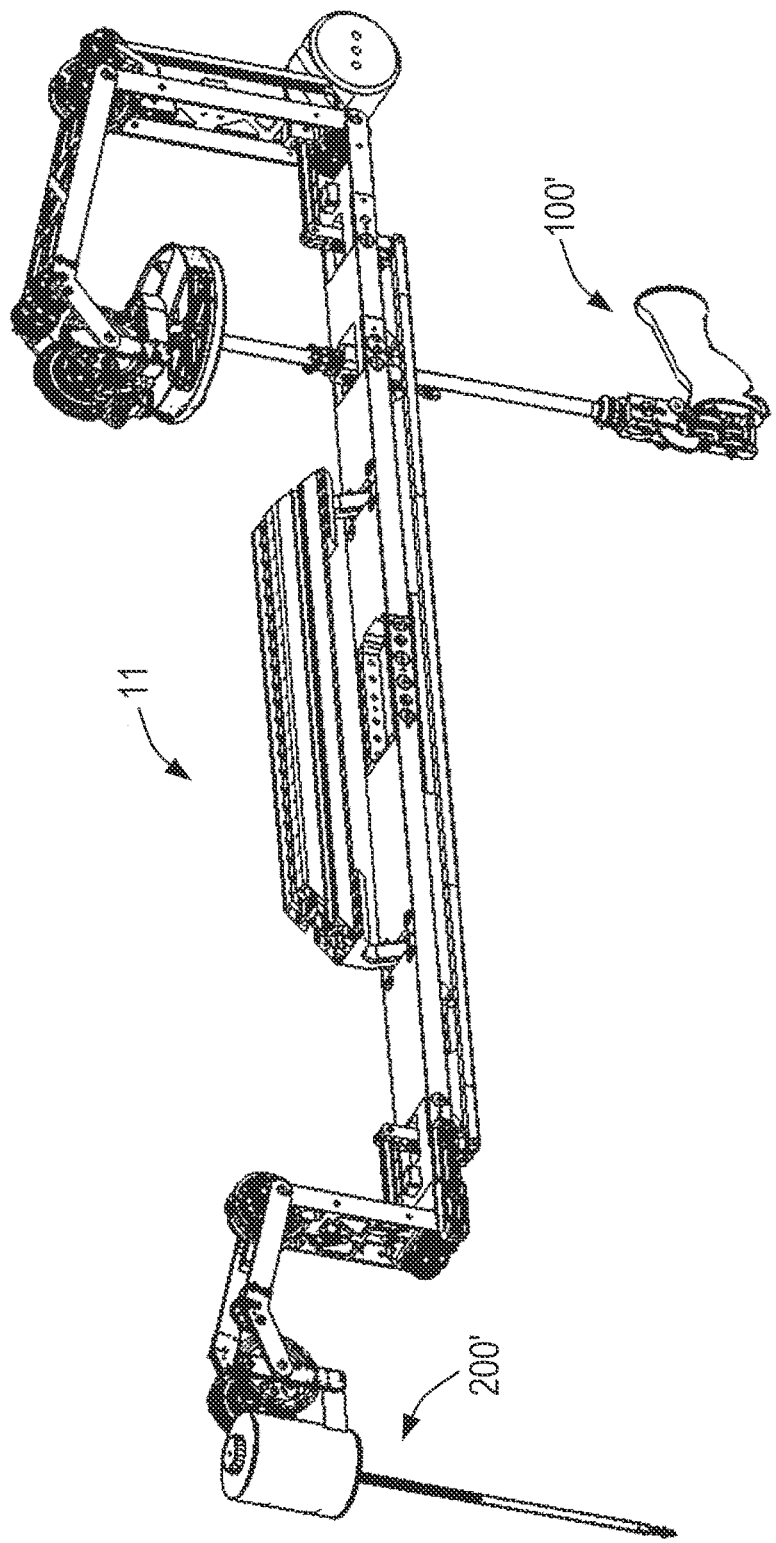
FIGS. 1C and 1D show additional exemplary teleoperated surgical robots having the translational instrument interface of FIG. 1A.

As shown in FIG. 1C, translational instrument interface 200' may be attached to and operated by mechanical teleoperated surgical instrument 11. Translational instrument interface 200' of FIG. 1C is constructed similar to translational instrument interface 200 of FIG. 1A. The exemplary master-slave configuration of FIG. 1C is described in U.S. Patent Application Publication No. 2014/0195010 to Beira, the entire contents of which are incorporated herein by reference, and previously-incorporated WO 2016/162752 to Beira. Similar to teleoperated surgical instrument 10, the macro movements in the translation degrees-of-freedom, e.g., left/right, upward/downward, inward/outward, of teleoperated surgical instrument 11 are actuated mechanically, whereas the micro movements in the articulation degrees-of-freedom, e.g., pitch and yaw, and the micro movements in the actuation degree-of-freedom, e.g., open/close, of translational instrument interface 200' are actuated electromechanically. As another example, translational instrument interface 200' is mechanical e.g., actuated via translational rigid link-driven transmission, hydraulic cylinders, or pneumatic elements, such that the translation degrees-of-freedom, e.g., left/right, upward/downward, inward/outward, are actuated mechanically and the articulation degrees-of-freedom, e.g., pitch and yaw, as well as the actuation degree-of-freedom, e.g., open/close, are actuated mechanically. Additionally, the rotation degree-of-freedom, e.g., pronosupination, of teleoperated surgical instrument 11 may be actuated either electromechanically or mechanically via a one or more cables and pulleys extending between handle 100' and translational instrument interface 200'. Accordingly, in various examples, teleoperated surgical instrument 11 with translational instrument interface 200' has (i) seven degrees-of-freedom actuated mechanically, (ii) four degrees-of-freedom actuated mechanically and three degrees-of-freedom actuated electromechanically, or (iii) three degrees-of-freedom actuated mechanically and four degrees-of-freedom actuated electromechanically. In the examples where teleoperated surgical instrument 11 has the three translational degrees-of-freedom actuated mechanically and the three articulation/actuation degrees-of-freedom actuated electromechanically, teleoperated surgical instrument 11 provides the advantages of electromechanically controlled micro movements and the advantages of mechanically controlled macro movements.

Figure 1D:
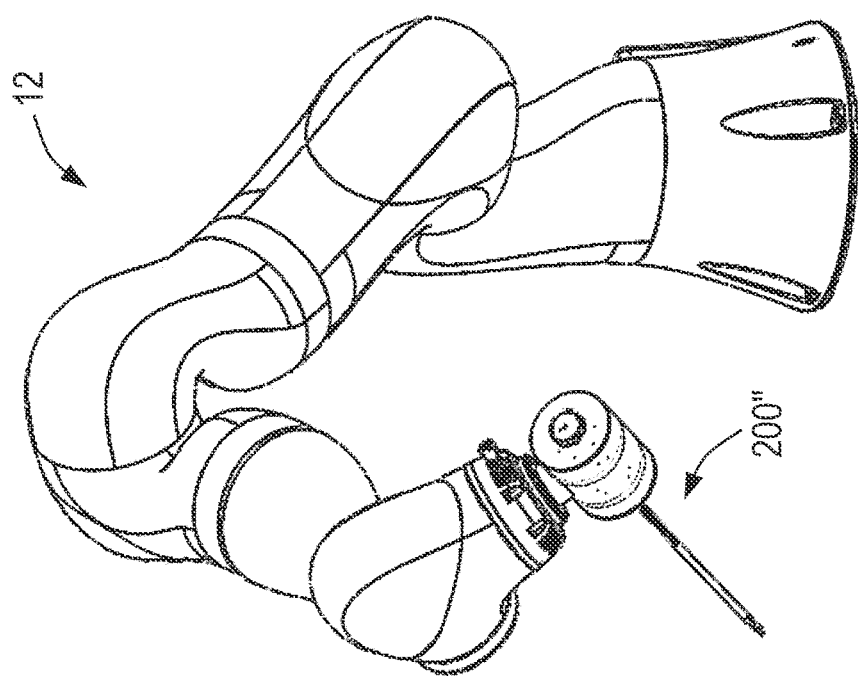

As shown in FIG. 1D, translational instrument interface 200" may be attached to and operated by robotic slave unit 12 of an electromechanical teleoperated surgical instrument. As will be understood by one skilled in the art, robotic slave unit 12 may be electrically coupled, e.g., via electrical wiring extending from robotic slave unit 12, to a master unit of the electromechanical teleoperated surgical instrument having a handle (not shown). Translational instrument interface 200" of FIG. 1D is constructed similar to translational instrument interface 200 of FIG. 1A. Accordingly, the translation degrees-of-freedom, e.g., left/right, upward/downward, inward/outward, the articulation degrees-of-freedom, e.g., pitch and yaw, the actuation degree-of-freedom, e.g., open/close, and the rotation degree-of-freedom, e.g., pronosupination, are actuated electromechanically. Accordingly, in various examples, teleoperated surgical instrument 12 with translational instrument interface 200" has seven degrees-of-freedom actuated electromechanically.

Figure 2:
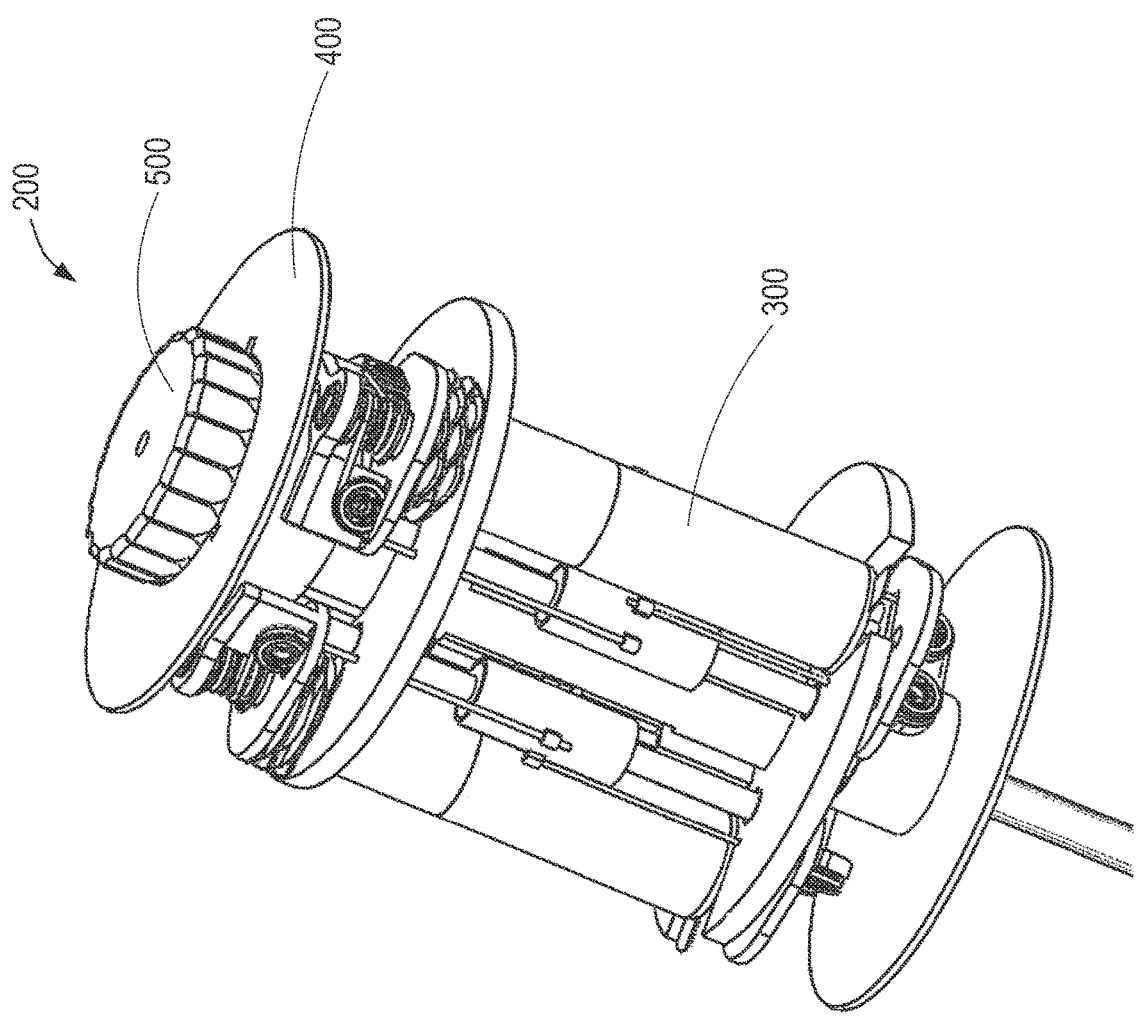
FIG. 2 shows a partial view of an exemplary translational instrument interface constructed in accordance with the principles of the present invention.

Referring now to FIG. 2, an exemplary translational instrument interface constructed in accordance with one aspect of the present invention is described. Translational instrument interface 200 is designed to be mounted to distal end 40 of slave unit 30 of teleoperated surgical instrument 10. Translational instrument interface 200 illustratively includes slave hub 300, sterile shield 400, and instrument 500. As shown in FIG. 2, sterile shield 400 is inserted within a lumen of slave hub 300, and instrument 500 is inserted within a lumen of sterile shield 400, such that sterile shield 400 provides a sterile, mechanical connection between slave hub 300 and instrument 500. Sterile shield 400 is removably coupled to slave hub 300, and instrument 500 is removably coupled to sterile shield 400. In this manner, sterile shield 400 and instrument 500 may be inserted into, and removed from slave hub 300 to insert and exchange instrument 500 during a surgical procedure, and to insert and remove sterile shield 400 before and after surgical use, respectively. In this manner, a used surgical instrument may be removed and exchanged for an unused surgical instrument for performing another surgery, now with the unused surgical instrument.

Figure 3:
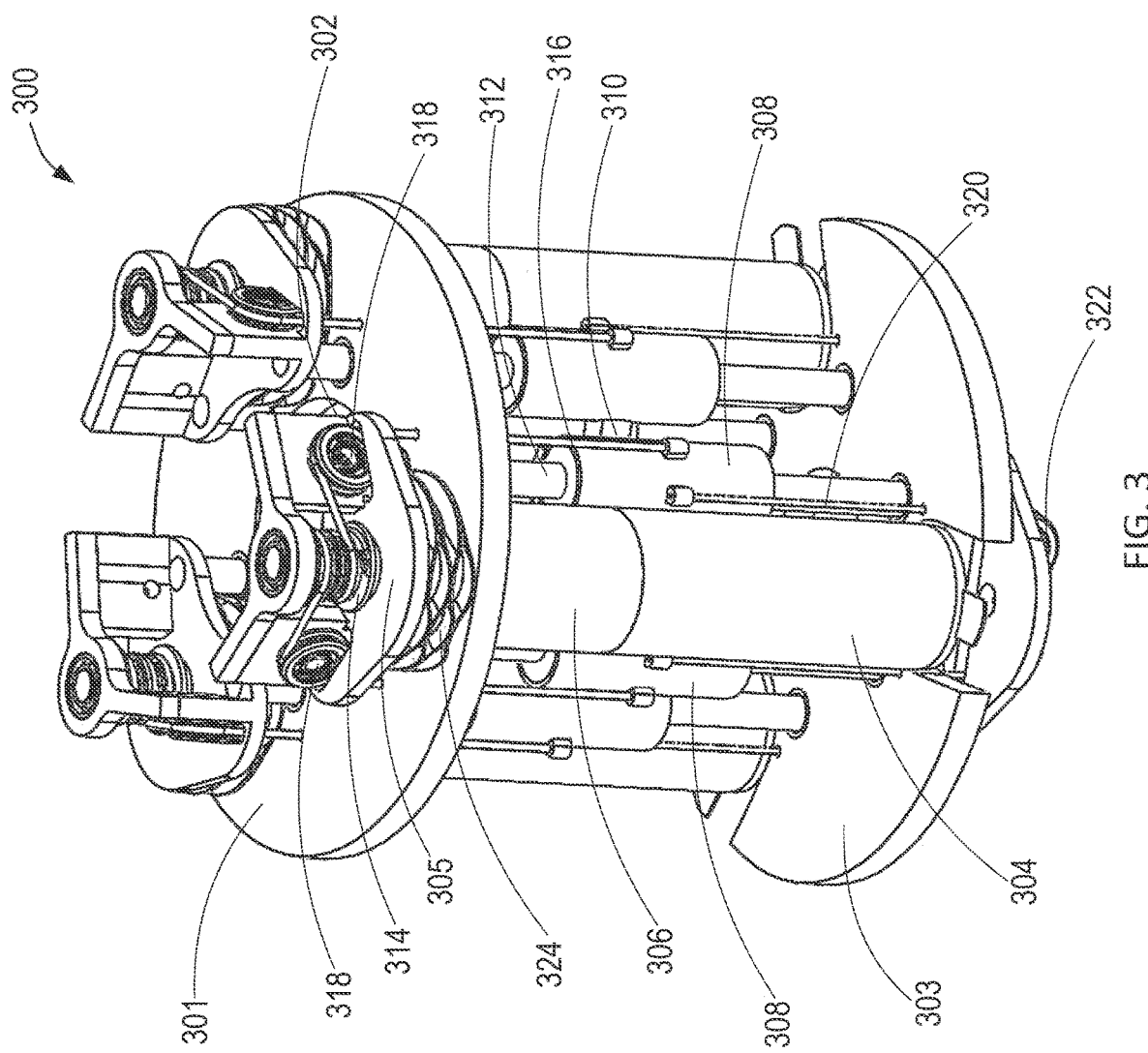
FIG. 3 shows the exemplary slave hub of the translational instrument interface of FIG. 2.

Referring now to FIG. 3, an exemplary slave hub constructed in accordance with one aspect of the present invention is described. Slave hub 300 may be mounted to the distal end of slave unit 30, such as those of the teleoperated surgical instruments described herein, so that slave hub 300 is rotatable about its longitudinal axis, e.g., pronosupination. Slave hub 300 preferably includes lumen 302 sized and shaped to receive sterile shield 400, and drive unit 304 for actuating movement of end-effector 506 of instrument 500 in one or more degrees-of-freedom.

Drive unit 304 illustratively includes three individual drive units, each for controlling one of three degrees-of-freedom. In the example of a serial kinematics of end-effector 506, one drive unit may actuate the end-effector to open and/or close, another drive unit may articulate pitch of the end-effector, and the other drive unit may articulate yaw of the end-effector. In the example of a serial-parallel kinematics of end-effector 506, one drive unit may articulate the end-effector to yaw, and two drive units, each controlling one blade of end-effector 506, may actuate the end-effector to perform the pitch articulation. In one embodiment, drive unit 304 includes a fourth drive unit that articulates pronosupination of the end-effector. Given that the individual drive units may be structurally and functionally identical, and as the degree-of-freedom actuated depends on the arrangement of components of the end-effector, the description hereafter will refer to drive unit 304 as representative of each individual drive unit.

In FIG. 3, slave hub 300 includes upper plate 301 and lower plate 303 such that drive unit 304 extends from one side of upper plate 301, in between upper plate 301 and lower plate 303, to an opposite side of lower plate 303. Drive unit 304 includes motor 306 and linear pointer 308 coupled to receptacle 310. Motor 306 is preferably electrically coupled to handle 100 via, e.g., electric wires and a control system, such that actuation of handle 100 via its user interface causes motor 306 to operate in accordance with the principles of the present invention. For example, motor 306 may cause linear pointer 308 to move translationally along rod 312 by causing driver pulley 314 to rotate, wherein driver pulley 314 is kinematically connected to linear pointer 308 via cable 316, e.g., flexible elements such as metallic or polymer cables, or semi-rigid elements such as a metal band. Drive unit 304 may include pulley 318 for converting motion of cable 316 due to axial rotation of driver pulley 314 to translational motion to translationally move linear pointer 308.

Linear pointer 308 may have two individual linear pointers such that each linear pointer is kinematically connected to driver pulley 314 via respective cables or bands, and pulleys, and wherein each linear pointer moves in an opposite direction to one another, e.g., when driver pulley 314 causes one linear pointer moves in one direction, the other linear pointer moves an equivalent amount in an opposite direction. In one embodiment, the two linear pointers are coupled to driver pulley 314 via a single cable. Thus, each drive unit may actuate movement of two receptacles via the two linear pointers of linear pointer 308. Linear pointer 308 is designed to move linearly along rod 312 responsive to actuation of motor 306. In one embodiment, the linear pointers are hydraulic or pneumatic pistons that move linearly.

Prior to insertion of instrument 500 into the lumen of sterile shield 400 within lumen 302 of slave hub 300, slave hub 300 may maintain a minimum "off-use" tension to keep cable 316 in its proper pathway and prevent unraveling. For example, a minimum "off-use" tension may be achieved by closing the loop of cable 316 by applying a force to linear pointer 308 via cable 320, e.g., a metallic or polymeric cable, and pulley 322. Pulley 322 may be disposed on the opposite side of lower plate 303 such that cable 320 extends from one of the linear pointers, over pulley 322, to the other linear pointer of liner pointer 308, thereby biasing linear pointer 308 toward lower plate 303.

When instrument 500 is inserted into sterile shield 400 within lumen 302 of slave hub 300, as described in further detail below, slave hub 300 may have an "in-use" tension such that translational instrument interface 200 may have enough rigidity to ensure force may be transmitted from slave hub 300 to instrument 500. The "in-use" tension may be much higher than the minimum "off-use" tension. This "in-use" tension may be provided by spring 324 disposed on one side of upper plate 301, in between upper plate 301 and drive plate 305. For example, prior to insertion of instrument 500 into the lumen of sterile shield 400 within lumen 302 of slave hub 300, spring 324 may be in a released, uncompressed state. Upon insertion of instrument 500 into the lumen of sterile shield 400, engagers of instrument 500 contact with linear pointers 308 applying a force to drive unit 304 in the direction of lower plate 303. This force compresses spring 324, setting cables 316 of slave hub 300 and force transmitting elements of instrument 500 under proper tension and alignment.

Figure 4:
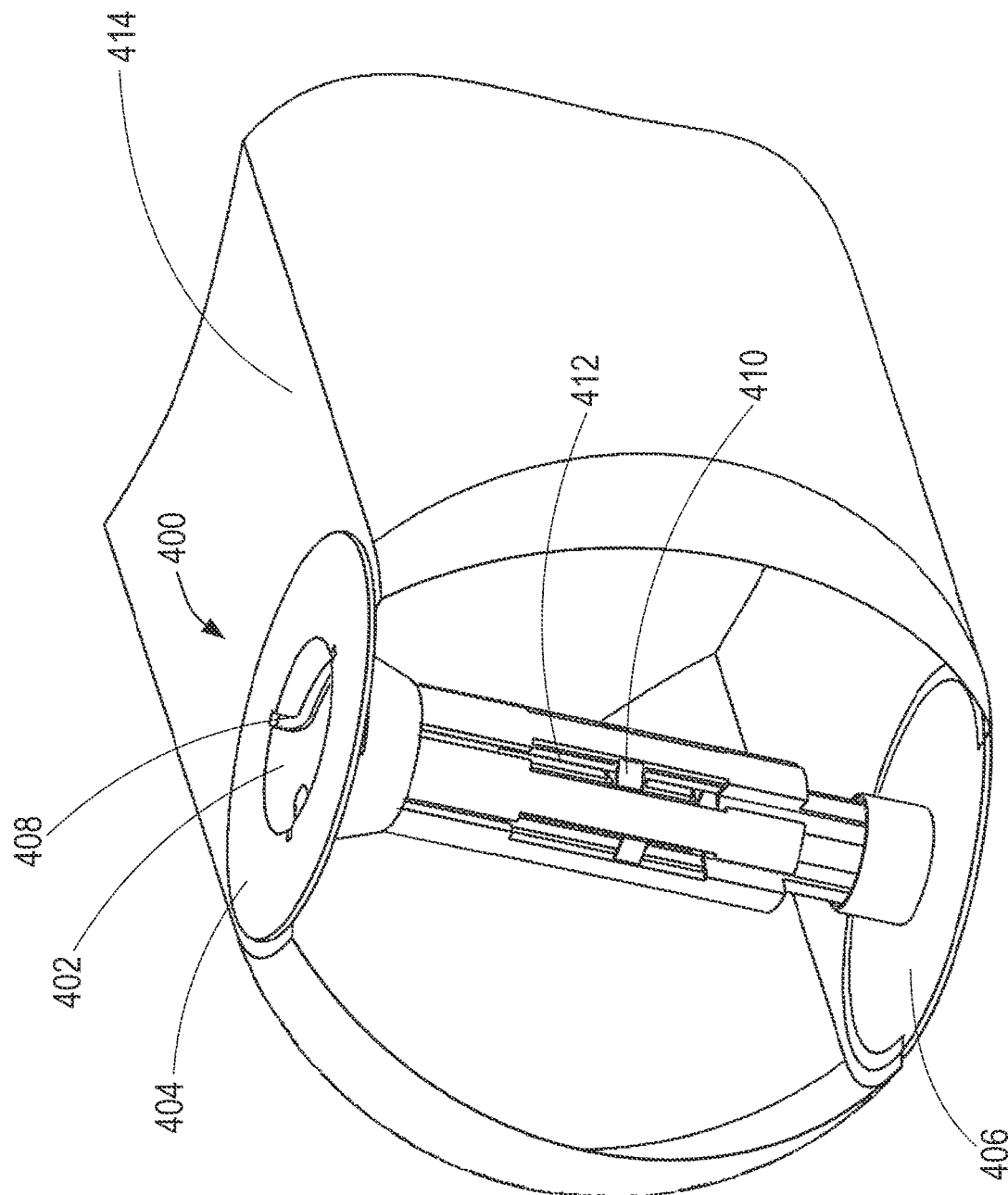
FIG. 4 shows the exemplary sterile shield of the translational instrument interface of FIG. 2.

Referring now to FIG. 4, an exemplary sterile shield constructed in accordance with one aspect of the present invention is described. Sterile shield 400 is sized and shaped to isolate the non-sterile slave hub 300 from sterile instrument 500 in the sterile environment and may have upper component 404 and lower component 406. In this manner, instrument 500 remains sterile throughout a surgical procedure and then may be reprocessed, or disposed of after a single use. Sterile shield 400 also may be disposable after a single use, although sterile shield 400 may be re-sterilized and reused after a surgical procedure. Advantageously, the portions of the teleoperated surgical instrument that contact tissue during surgery (preferably only instrument 500), are disposable while the more complicated, expensive components of the teleoperated surgical instrument are reusable.

Sterile shield 400 includes lumen 402 sized and shaped to receive instrument 500 therein. Upper component 404 may be received by an upper end of lumen 302 of slave hub 300, e.g., proximal to upper plate 301. Lower component 406 may be received by a lower end of lumen 302 of slave hub 300, e.g., proximal to lower plate 303. Upper component 404 is shaped to engage with lower component 406 to form the sterile barrier. Upper component 404 may include slit 408 within lumen 402, shaped and sized to permit locking engagement between instrument 500 and sterile shield 400. For example, slit 408 may be sized and shaped to permit a locking pin of instrument 500 to enter and rotate with the rotation of instrument 500 such that the locking pin travels along slit 408 to secure instrument 500 within lumen 402 of sterile shield 400, and to create a mechanical advantage that permits the compression of spring 324 such that the cables are put in "in-use" tension as described above.

Sterile shield 400 illustratively includes moveable slider 410, to provide a mechanical connection between receptacle 310 of slave hub 300 and the corresponding actuator of instrument 500, described in further detail below. Moveable slider 410 may move translationally along pathway 412 (e.g., in a slot), parallel to the longitudinal axis of sterile shield 400, dependent on the mechanical forces transmitted from slave hub 300 to instrument 500. Moveable slider 410 preferably includes an amount of individual slide elements corresponding with the amount of receptacles of slave hub 300. For example, when slave hub 300 has three drive units, each coupled to two linear pointers, slave hub 300 has six receptacles and accordingly, sterile shield 400 has six slide elements. Sterile shield 400 also may be integrated on sterile sleeve 414 to create a sterile barrier for the entire slave unit 30, or the entire teleoperated surgical instrument 10.

Figure 5A:
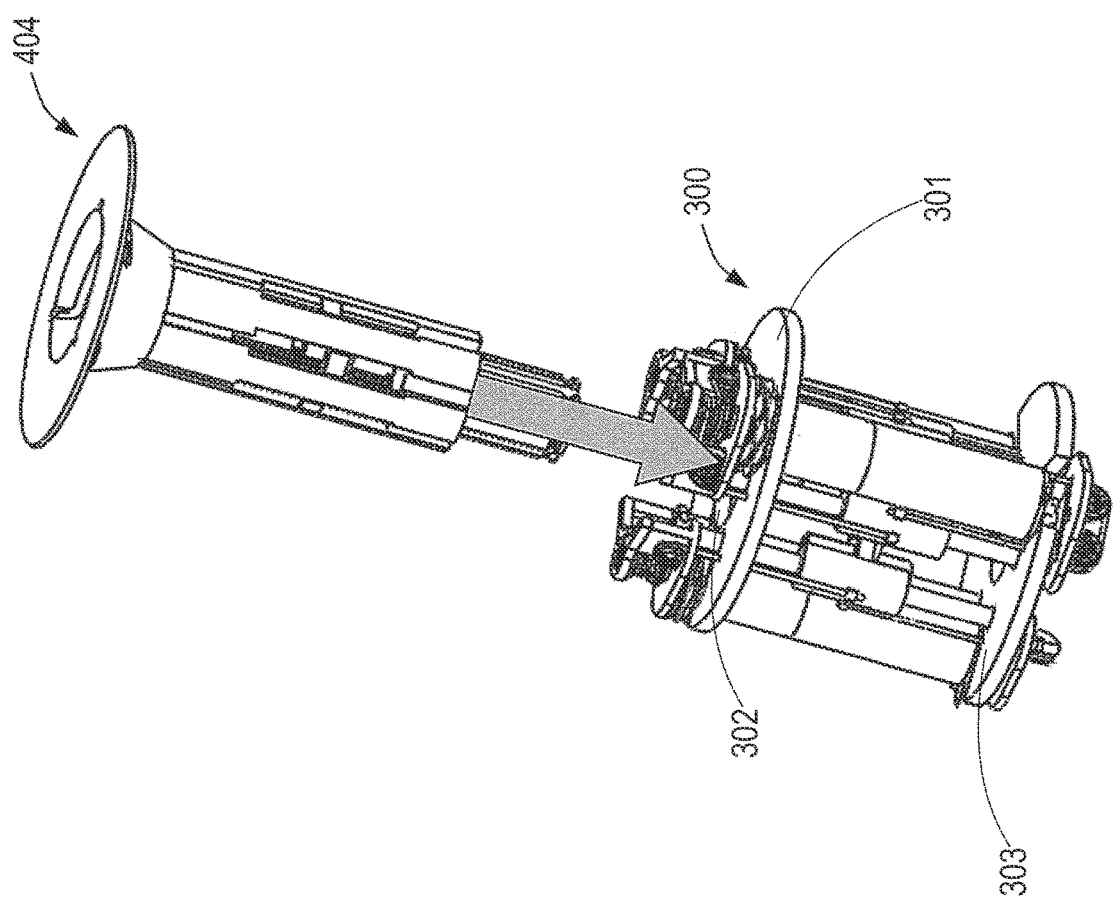
FIGS. 5A-C illustrate the insertion of the sterile shield of FIG. 4 into the slave hub of FIG. 3.
Figure 5B:
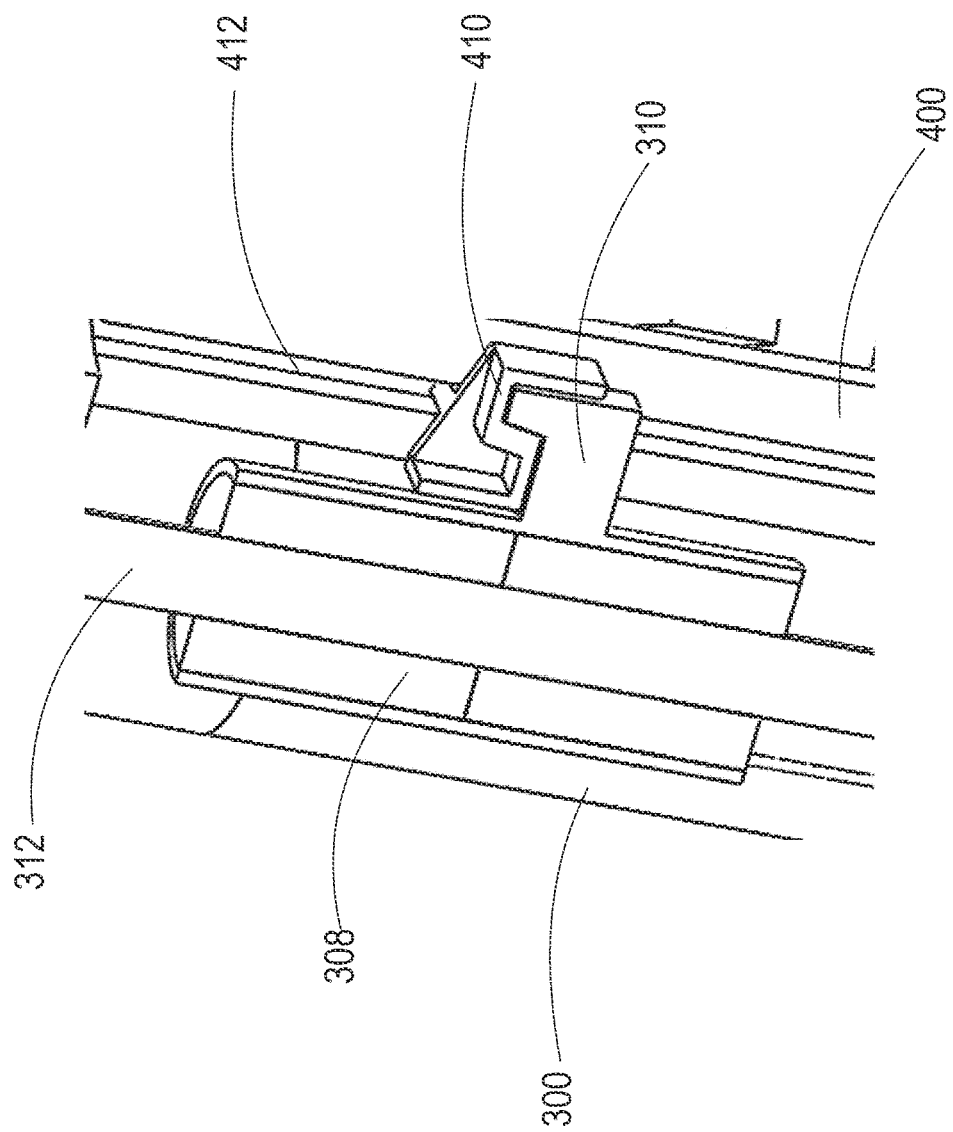
Figure 5C:
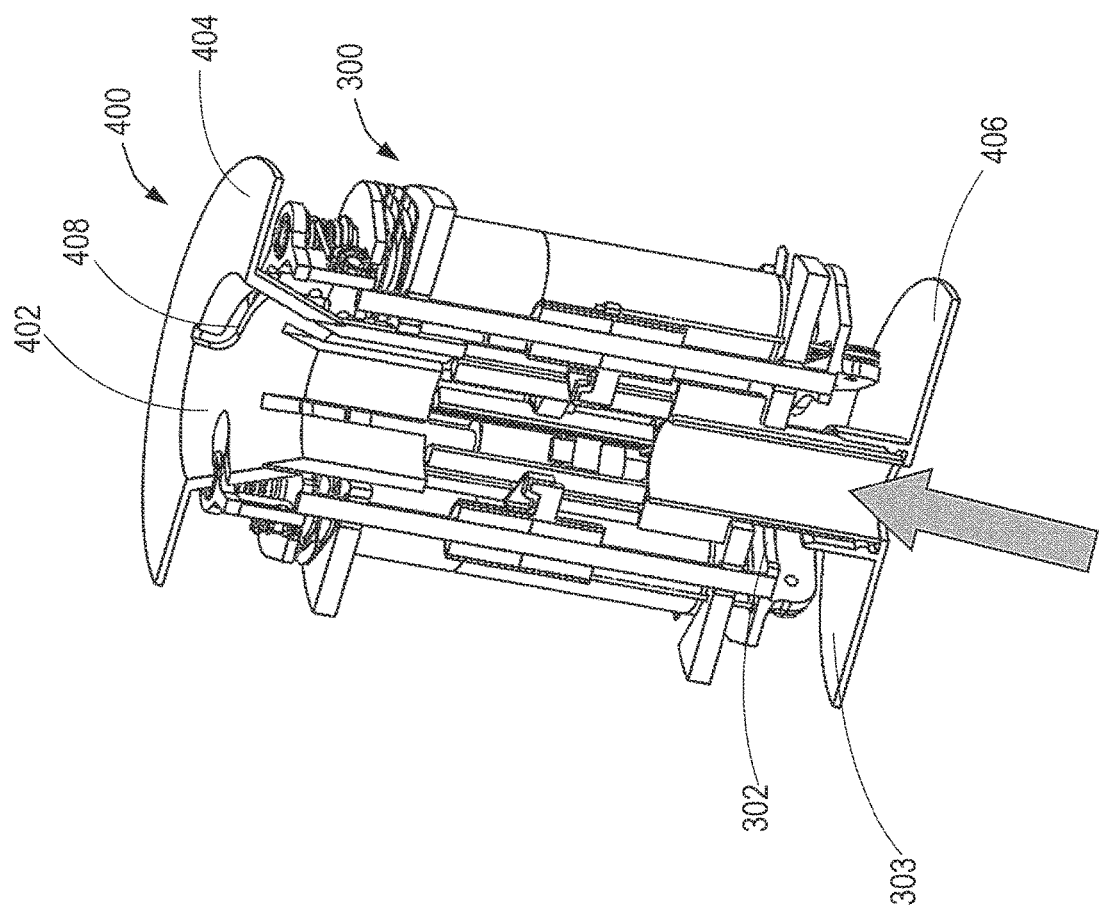

Referring now to FIGS. 5A-C, insertion of sterile shield 400 into slave hub 300 is described. As shown in FIG. 5A, upper component 404 of sterile shield 400 may be inserted through an upper end of lumen 302 of slave hub 300, e.g., proximal to upper plate 301, such that upper component 404 is positioned within lumen 302 of slave hub 300. Lumen 302 of slave hub 300 and upper component 404 may have a corresponding asymmetric shape, e.g., a water drop or asymmetrical triangle, such that upper component 404 may only be inserted through lumen 302 in a specific axial orientation.

As shown in FIG. 5B, when upper component 404 of sterile shield 400 is positioned within lumen 302 of slave hub 300, receptacle 310 engages with one side, e.g., bottom side, of moveable slider 410. As shown in FIG. 5B, moveable slider 410 and receptacle 310 may have a cross-sectional shape that maximizes transmission of mechanical force from receptacle 310 to moveable slider 410, e.g., receptacle 310 may have a hook shape whereas moveable slider 410 may have an S-shaped cross-section to engage with receptacle 310 on one side, and a corresponding actuator of instrument 500 on the other, as described in further detail below. As will be understood by one skilled in the art, moveable slider 410 and receptacle 310 could have other cross-sectional shapes to maximize transmission of mechanical force from receptacle 310 to moveable slider 410. Accordingly, as linear pointer 308 moves along rod 312 of slave hub 300, receptacle 310 will apply a mechanical force on moveable slider 410, such that both moveable slider 410 and receptacle 310 will move translationally along pathway 410 of sterile shield 400.

As shown in FIG. 5C, lower component 406 of sterile shield 400 is insertable through a lower end of lumen 302 of slave hub 300, e.g., proximal to lower plate 303, such that lower component 406 is positioned within lumen 302 of slave hub 300 and engages with upper component 404. For example, lower component 406 may snap into upper component 404 to create a sterile barrier. In another example, lower component 406 may be rotated into upper component 404 creating a locking engagement with upper component 404 such that upper component 404 cannot rotate relative to lumen 302 of slave hub 300. Accordingly, upon insertion of instrument 500 into lumen 402 of sterile shield 400, the rotation of instrument 500 required to have the locking pins travel along slit 408 to secure instrument 500 within lumen 402, as described in further detail below, does not result in a rotation of upper component 404 of sterile shield 402. Lumen 302 of slave hub 300 and lower component 406 may have a corresponding asymmetric shape, a water drop or asymmetrical triangle, such that lower component 406 may only be inserted through lumen 302 in a specific axial orientation.

Figure 6A:
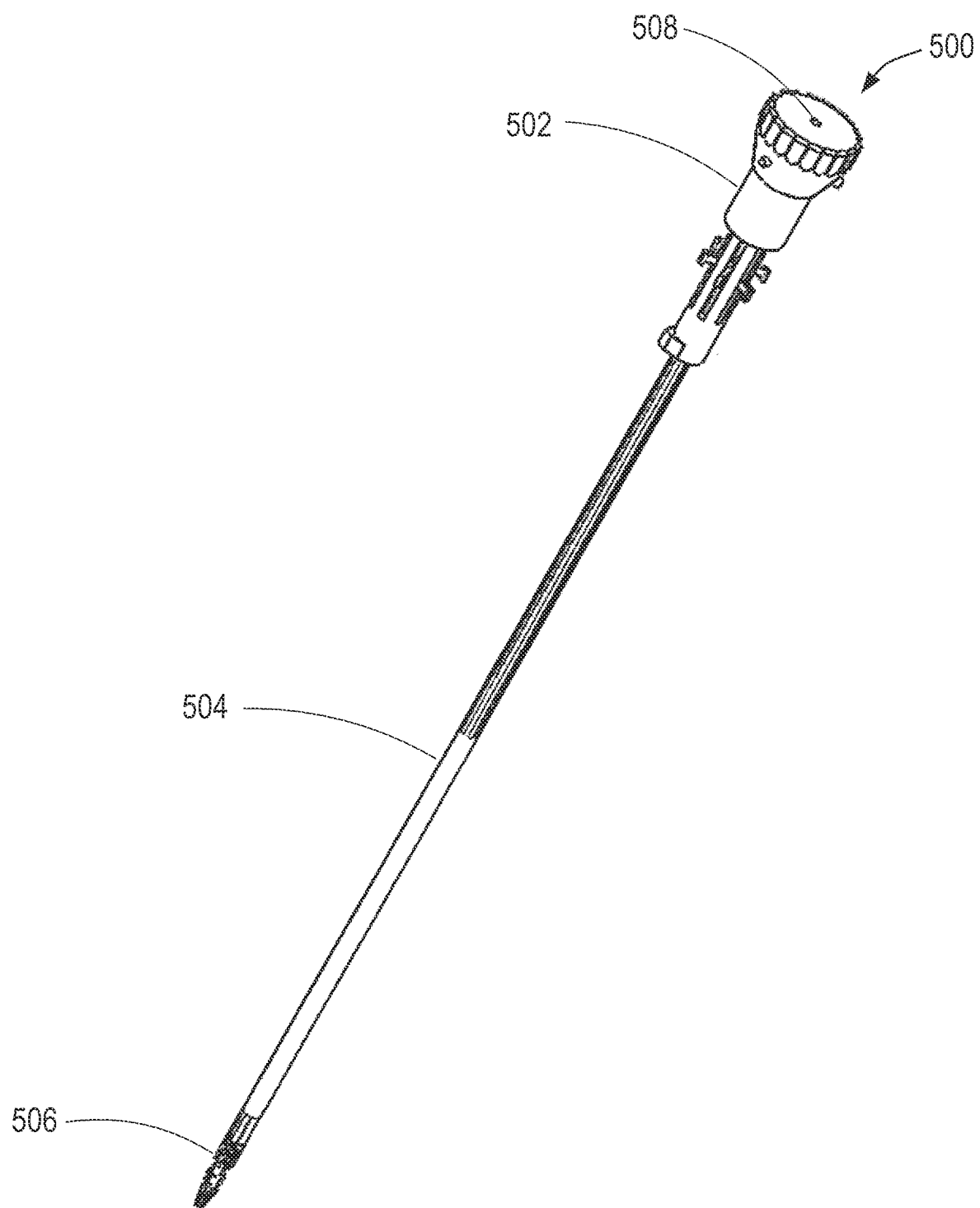
FIG. 6A shows the exemplary instrument of FIG. 2, FIGS. 6B-C show the instrument head of FIG. 6A.

Referring now to FIG. 6A, an exemplary instrument constructed in accordance with one aspect of the present invention is described. As shown in FIG. 6A, instrument 500 illustratively includes head 502 at a proximal region of instrument 500, end-effector 506 at a distal region of instrument 500 and shaft 504, which is preferably elongated, extending therebetween. Instrument 500 also may include lumen 508 extending through head 502 and shaft 504. In one embodiment, lumen 508 only extends through shaft 504. Instrument 500 is sized and shaped to be inserted through lumen 402 of sterile shield 400, and linearly engage with slave hub 300 such that a force by slave hub 300 is translationally transmitted to instrument 500 to actuate movement of end-effector 506 in one or more degrees-of-freedom, e.g., one, two, three or four degrees-of-freedom. Instrument 500 may be reusable but is preferably disposable after a single use. Instrument 500 may not require any degrees-of-freedom at end-effector 506, e.g. monopolar hooks used in electrosurgery.

Figure 6B:
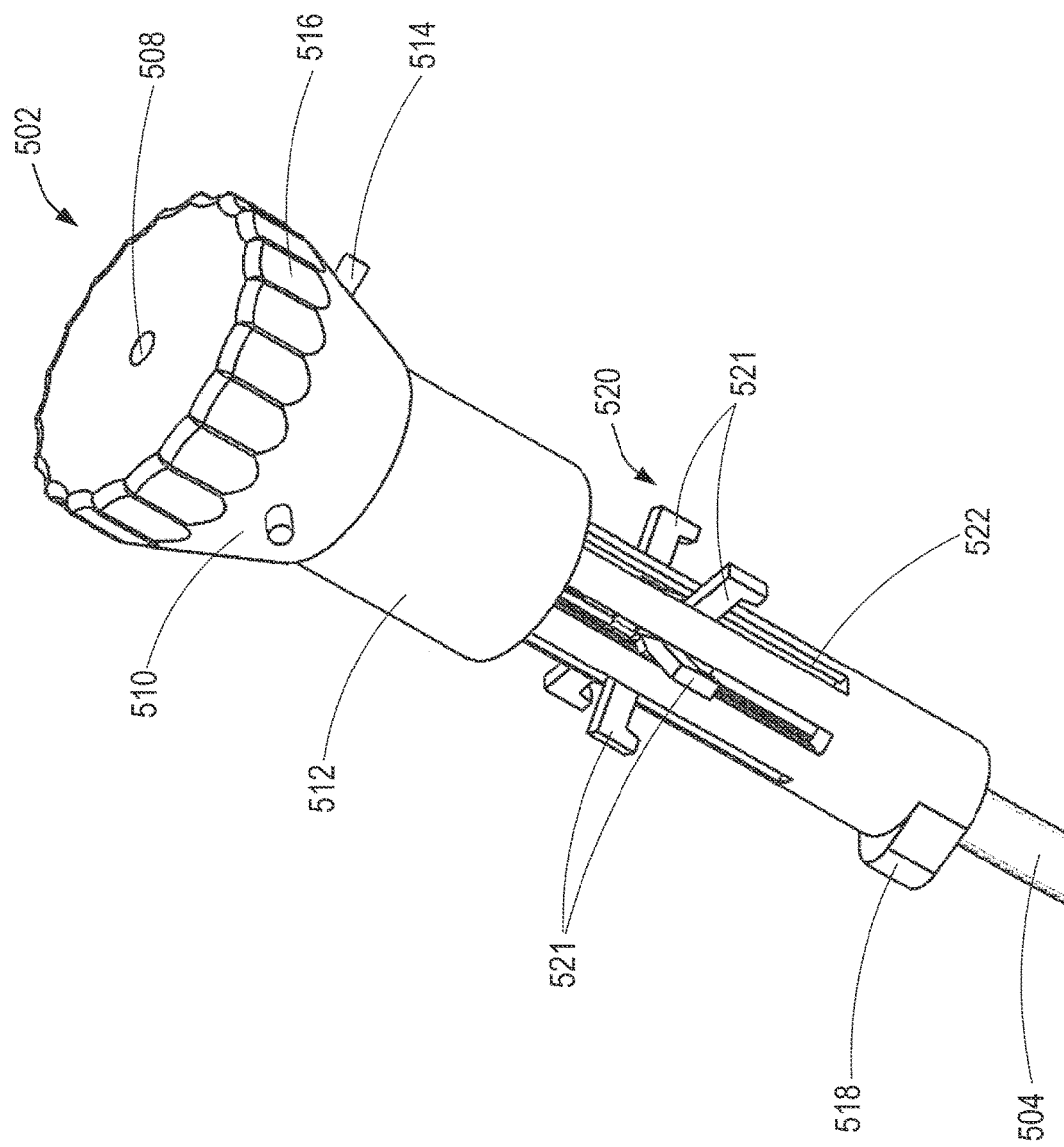
FIG. 6D shows the end-effector of FIG. 6A.
Figure 6C:
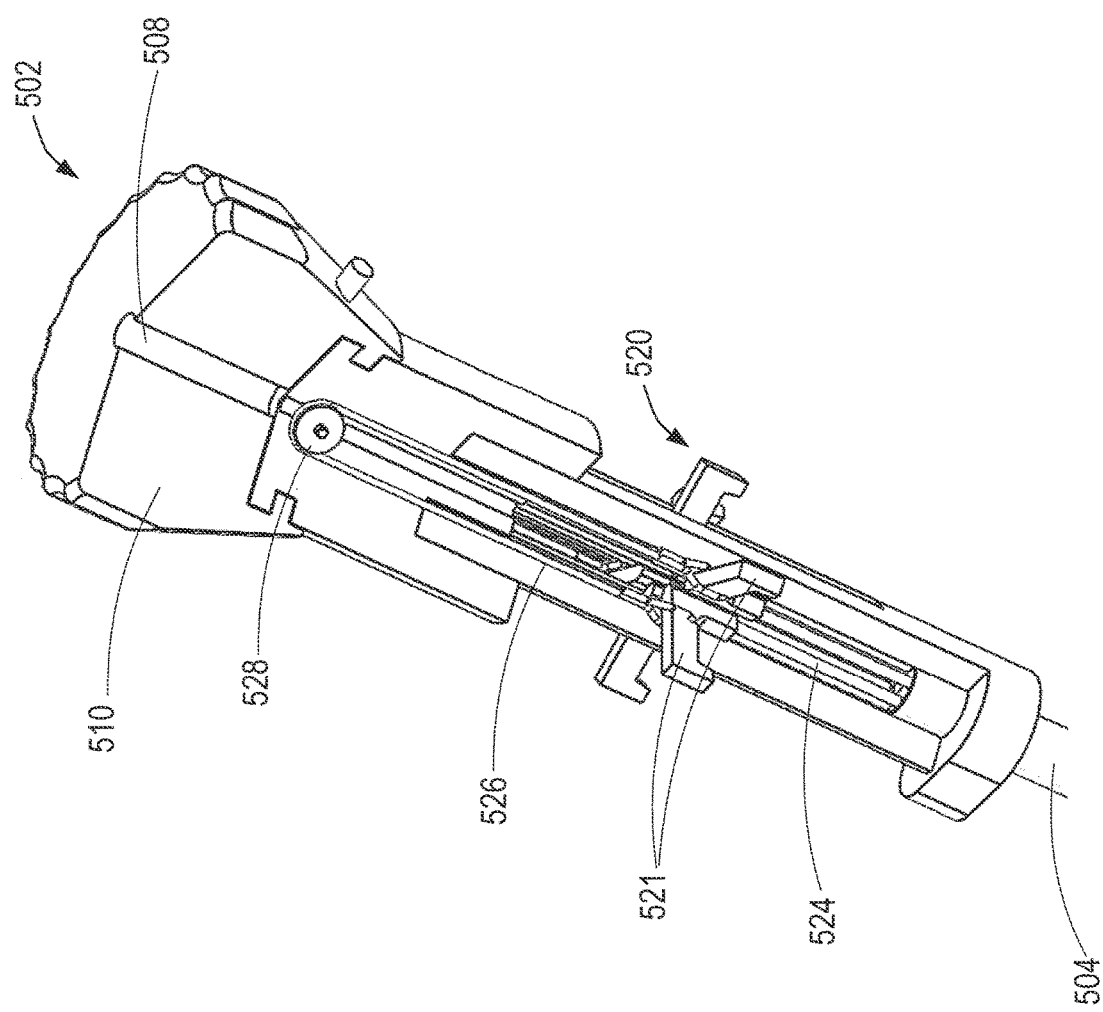

Referring now to FIGS. 6B-6C, head 502 is described in further detail. As shown in FIG. 6B, head 502 includes lumen 508 extending therethrough. Lumen 508 may be sized and shaped to receive electrical cables electrically coupled to the electrosurgical generators when end-effector 506 has electrosurgical instruments. Head 502 may have rotatable portion 510 and fixed portion 512. Rotatable portion 510 rotates relative to fixed portion 512 about the longitudinal axis of instrument 500, e.g., when instrument 500 is positioned within lumen 402 of sterile shield 400. Rotatable portion 510 may include locking pins 514 sized and shaped to enter slit 408 of upper component 404 of sterile shield 400 such that rotation of rotatable portion 510 causes locking pins 514 to enter slit 408 and secure instrument 500 within sterile shield 400. As will be understood by one skilled in the art, locking pins 514 may have any shape that may effectively secure instrument 500 within sterile shield 400. Rotatable portion 510 may have grooves 516 along the surface of rotatable portion 510 such that an operator of teleoperated surgical instrument 10 may achieve an enhanced grip and rotate rotatable portion 510 easier.

Head 502 may include key 518, e.g., a puka-yoke, shaped and sized such to ensure proper axial alignment of instrument 500 within sterile shield 400. Accordingly, lumen 402 of sterile shield 400 includes a channel for receiving key 518 as instrument 500 is inserted within sterile shield 400.

In one embodiment, head 502 has an identification tag, e.g., RFID or barcode, configured to store information regarding instrument 500, e.g., instrument type, serial number, calibration data, range-of-motion, end-effector kinematics such as numbers and types of degrees-of-freedom including serial-serial, serial-parallel, yaw-pitch-actuate, pitch-yaw-actuate, roll-pitch-yaw-actuate, pitch-roll-actuate, etc., or controlling offsets. Such instrument information may be detected from the identification tag via a control system of the teleoperated surgical instrument by scanning the identification tag and/or electrically coupling the teleoperated surgical instrument to instrument 500.

Head 502 preferably includes actuator 520 permitted to move translationally responsive to user input at the handle of the teleoperated surgical instrument to actuate movement at the end-effector in multiple degrees-of-freedom. Preferably, actuator 520 is coupled to slave hub 300, e.g., via sterile shield 400, and translational movement at slave hub 300 causes the translational movement at actuator 520. For example, actuator 520 may include a plurality of engagers 521 that independently move translationally along corresponding linear pathways 522 (e.g., slot in the proximal region of the shaft) responsive to translational movement at corresponding receptacles 310 of slave hub 300 coupled thereto, e.g., via corresponding sliders 410 of shield 400, caused by user input at the handle of the teleoperated surgical instrument. Actuator 520 is sized and shaped to contact moveable slider 410 of sterile shield 400 on a side opposite to that of receptacle 310 of slave hub 300. For example, actuator 520 may have a hook shape, or any other shape understood in the art to maximize transmission of force between receptacle 310 and actuator 520. Actuator 520 may be coupled to end-effector 506 via a plurality of force transmitting elements disposed within lumen 508 of shaft 504, as described in further detail below. When actuated, actuator 520 applies force to end-effector 506 via the force transmitting element(s) to move end-effector 506 in at least one degree of freedom. For example, actuator 520 may move in a translational manner, e.g., in a direction parallel to the longitudinal axis of elongated shaft 504, which in turn moves end-effector 506 via the force transmitting element couple therebetween.

In accordance with one aspect of the invention, instrument head 502 may have one standard size/diameter, whereas instrument shaft 504 and end-effector 506 have a range of diameters. Specifically, instrument head 502 may have a 10 mm diameter, whereas instrument shaft 504 and end-effector 506 may have diameters of 3 mm, 5 mm, 8 mm or 10 mm. Accordingly, slave hub 300 and sterile shield 400 may be sized and shaped to accept instruments having different diameters. Clinically, this allows for a range of tools to be used, depending on the procedure.

As shown in FIG. 6C, actuator 520 may be coupled to force transmitting element 524, e.g., rigid elements such as steel, composite or polymeric rods, flexible elements such as tungsten, steel, polymer, or Dyneema cables, wires or ropes, or semi-rigid elements such as a metal band, at one end, wherein force transmitting element 524 is coupled to a component of end-effector 506 at its other end such that actuation of actuator 520 actuates movement of end-effector 506 in one of three degrees-of-freedom. As is described above, actuator 520 also may include a plurality of engagers 521. For example, actuator 520 may include a first engager coupled to a first component of end-effector 506 via a first force transmitting element to move end-effector 506 in a first degree-of-freedom, e.g., open and close, responsive to force applied at the first engager, a second engager coupled to a second component end-effector 506 via a second force transmitting element to move end-effector 506 in a second degree-of-freedom, e.g., pitch, responsive to force applied at the second engager, and a third engager coupled to a third component of end-effector 506 via a third force transmitting element to move end-effector 506 in a third degree-of-freedom, e.g., yaw, responsive to force applied at the third engager. The forces applied to the first, second, and third engagers of actuator 520 may applied, e.g., via a first, second, or third hydraulic and/or a first, second, or third motor of the slave hub, responsive to user input at handle 100. In one embodiment, actuator 520 includes a fourth engager coupled to a fourth component of end-effector 506 via a fourth force transmitting element to move end-effector 506 in a fourth degree-of-freedom, e.g., pronosupination, responsive to force applied at the fourth engager, e.g., via a fourth hydraulic, one or more cables and pulleys extending from translational instrument interface 200 to handle 100, and/or a fourth motor electrically coupled to the user interface at the handle 100.

In accordance with one aspect, each engager 521 is independently actuatable responsive to user input applied at handle 100 of the surgical robot. For example, a user actuates actuator 520 responsive to user input applied at the user interface at handle 100 by, e.g., moving a three-dimensional joystick, which in turn activates a corresponding motor at slave hub 300 to translationally move engager 521 along the proximal end of instrument 500. e.g., parallel to the longitudinal axis of shaft 504. Such translational movement of engager 521 moves force transmitting element 524 coupled thereto which moves end-effector 506 in a degree-of-freedom.

As will be readily apparent to one skilled in the art, while a single engager is described for each degree-of-freedom, each engager may include a pair of engagers as illustrated. For example, three pairs of engagers may be used to control three degrees-of-freedom, each pair of engagers controlling a degree-of-freedom. Each pair of engagers is kinematically connected to the respective component of end-effector 506 via one or more force transmitting elements 524 that will control the respective degree-of-freedom. Each individual engager of a pair of engagers moves in an opposite direction to one another, e.g., when a receptacle applies a force to an engager causing the engager to move in one direction, the corresponding engager of the pair will move in an equivalent amount in an opposite direction. Thus, each drive unit of slave hub 300 may actuate movement of a pair of engagers via the two receptacles coupled to linear pointer 308.

Prior to insertion of instrument 500 into sterile shield 400, instrument 500 may maintain a minimum "off-use" tension to keep force transmitting element 524 in its proper pathway and prevent unraveling. For example, a minimum "off-use" tension may be achieved by closing the loop of force transmitting element 524 by applying a force to actuator 520 via cable 526, e.g., a metallic or polymeric cable, and pulley 528 disposed within head 502. Pulley 528 may be disposed toward rotatable portion 510 of head 502 such that cable 526 extends from one of the engagers, over pulley 528, to the another engager of a pair of engagers of actuator 520.

Figure 6D:
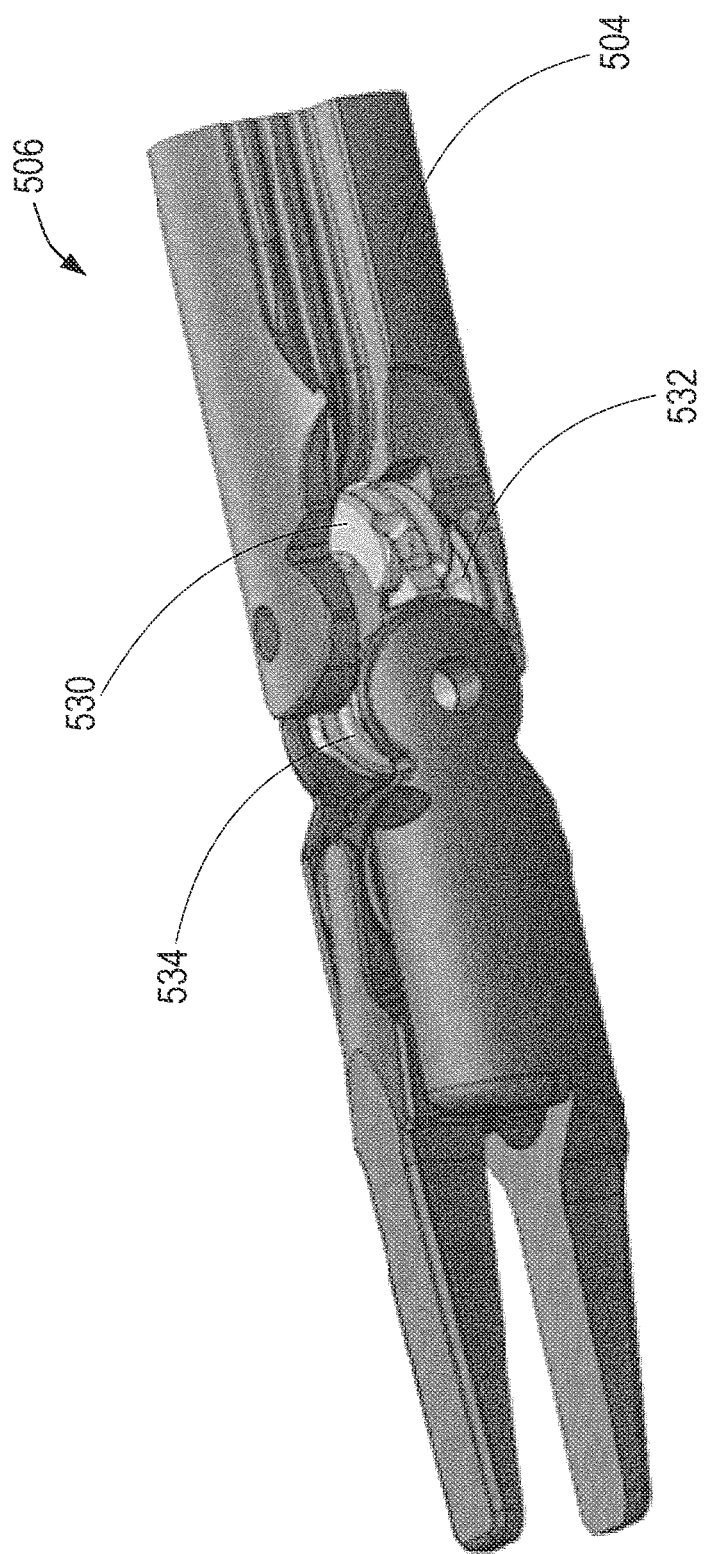

Referring now to FIG. 6D, an exemplary end-effector is described. Translational instrument interface 200 may be electrically coupled to handle 100 to connect the movement in the multiple degrees-of-freedom of end-effector 506 to movement controllability in the corresponding degrees-of-freedom of handle 100 such that end-effector 506 replicates the movements of handle 100 when teleoperated surgical instrument 10 is operated. As described above, each engager 521 of actuator 520 may be coupled to a respective component of end-effector 506 that will control the respective degree-of-freedom via respective pair of force transmitting elements 524. For example, the first engager may be coupled to yaw component 530 of end-effector 506 via an element of force transmitting element 524 such that actuation of the first engager will articulate the yaw degree-of-freedom of end-effector 506; a second engager may be coupled to pitch component 532 of end-effector 506 via an element of force transmitting element 524 such that actuation of the second engager will articulate the pitch degree-of-freedom of end-effector 506; and a third engager may be coupled to open and close component 534 of end-effector 506 via an element of force transmitting element 524 such that actuation of the third engager will actuate the open and close degree-of-freedom of end-effector 506. The pronosupination degree-of-freedom of end-effector 506 may be actuated via the master-slave configuration of teleoperated surgical instrument 10 such that a rotation of handle 100 causes slave unit 30 to rotate slave hub 300, e.g., via one or more cables and pulleys extending from handle 100 to slave hub 300, and effectively end-effector 506. In one embodiment, a fourth engager may be coupled to a pronosupination component of end-effector 506 via an element of force transmitting element 524 such that actuation of the fourth engager will articulate the pronosupination degree-of-freedom of end-effector 506.

Figure 7A:
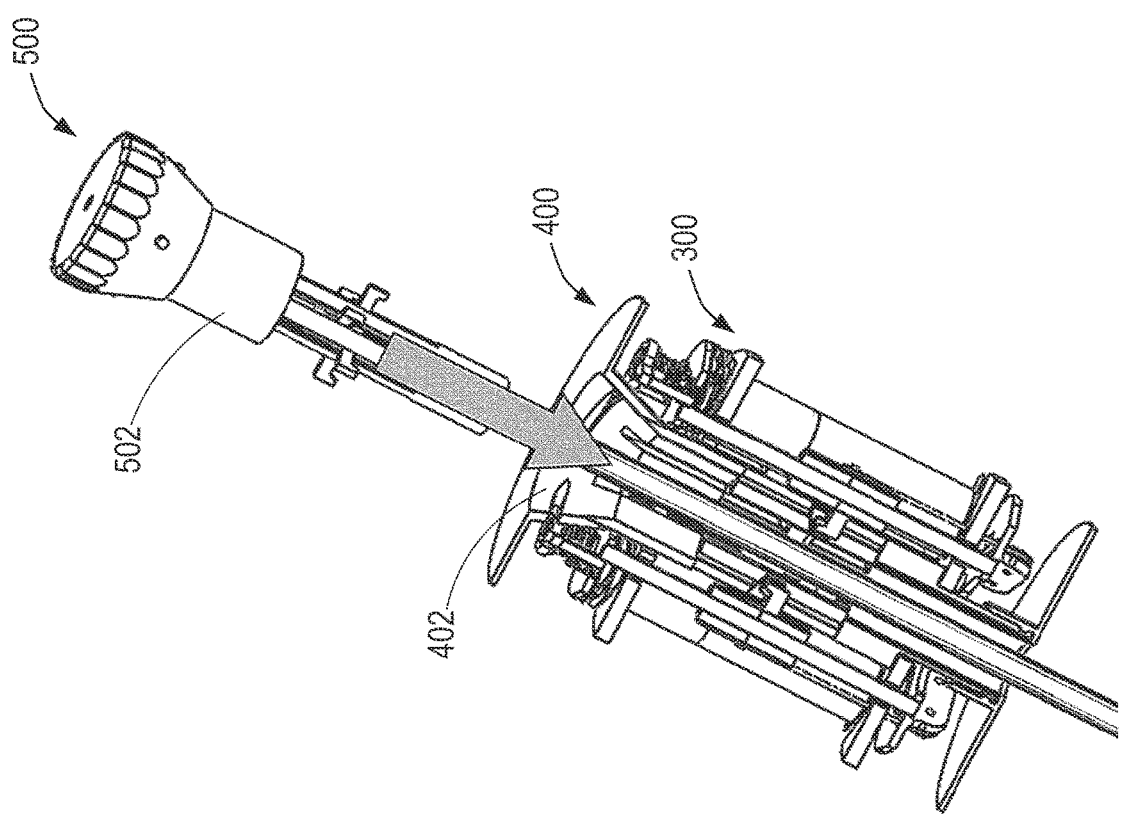
FIGS. 7A-C illustrate the insertion of the instrument of FIG. 6A into the sterile shield of FIG. 4 within the slave hub of FIG. 3.
Figure 7B:
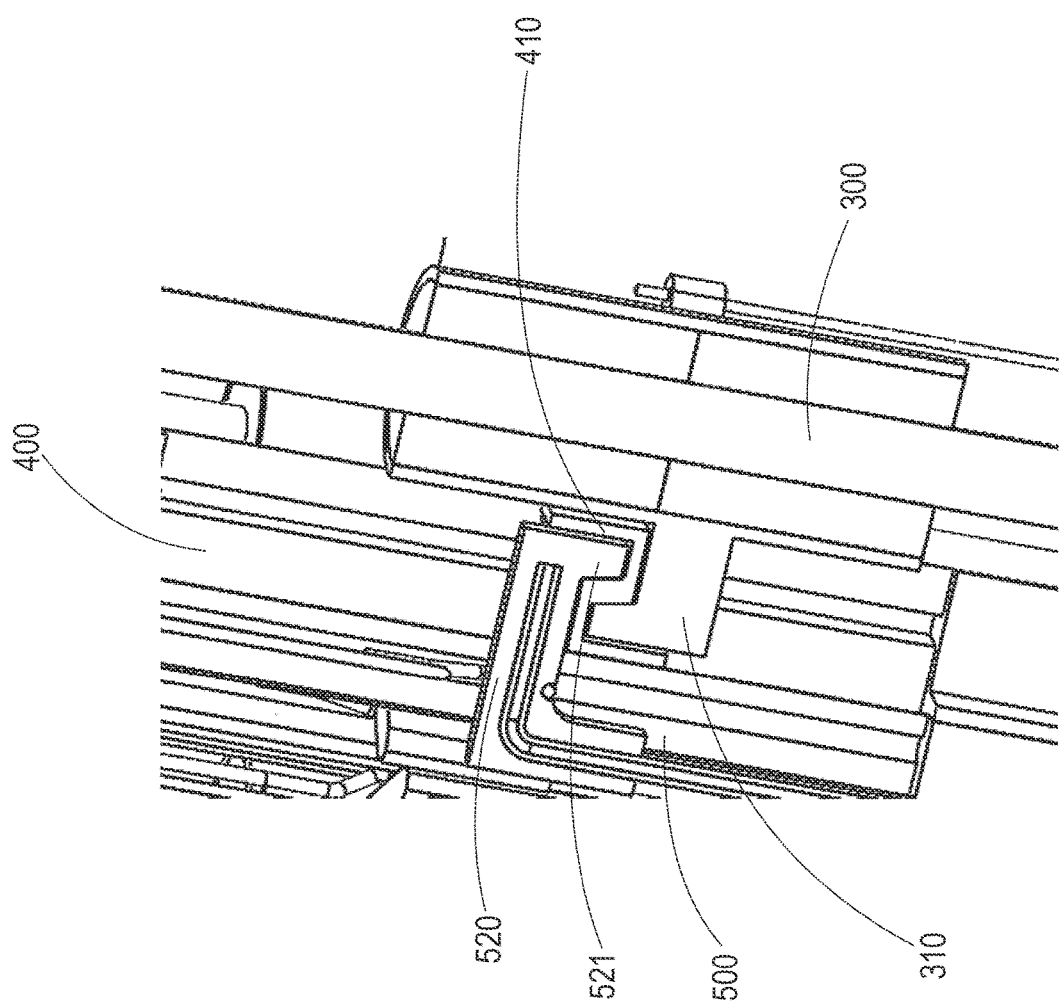
Figure 7C:
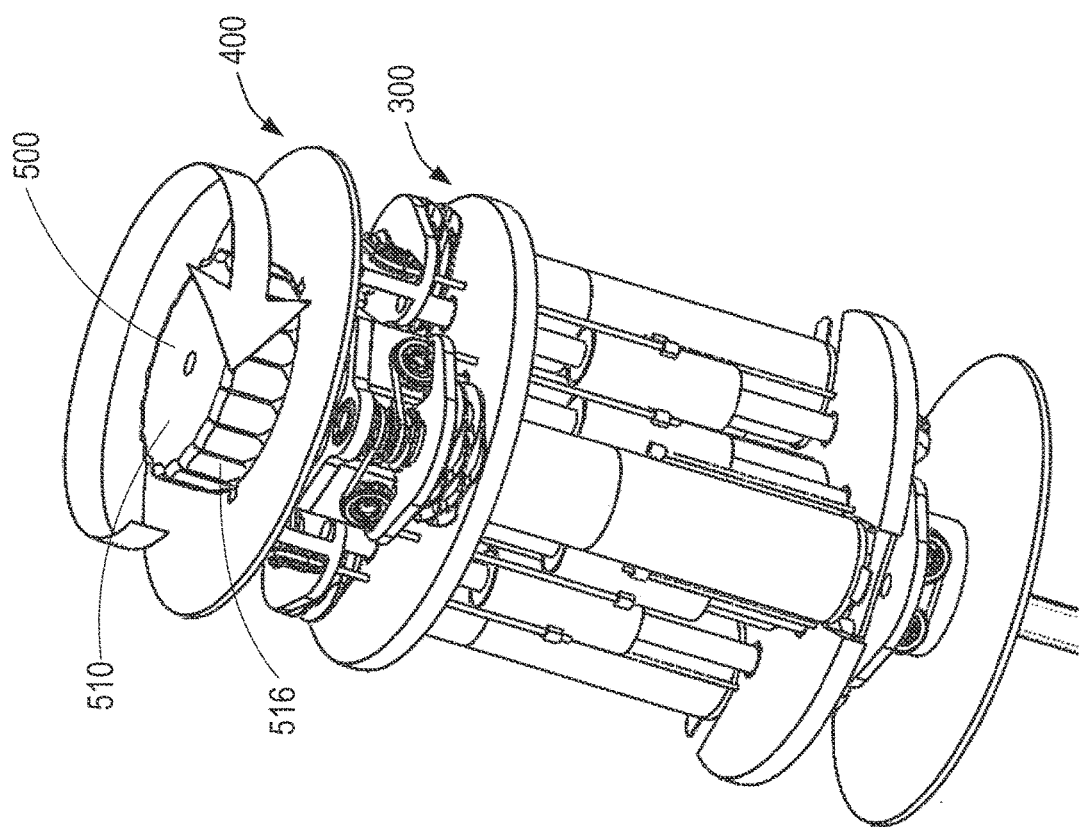

Referring now to FIGS. 7A-C, insertion of instrument 500 into sterile shield 400 within slave hub 300 is described. As shown in FIG. 7A, instrument 500 may be inserted within lumen 402 of sterile shield 400. As described above, instrument head 502 may include key 518 (not shown) such that instrument 500 may be properly aligned within sterile shield 400, e.g., each engager 521 of actuator 520 engages with the corresponding receptacle 310 of slave hub 300 and moveable slider 410 of sterile shield 400 as shown in FIG. 7B. As sterile shield 400 is positioned within lumen 302 of slave hub 300, at least one of the receptacles of receptacle 310 may not be in contact with the corresponding moveable slider 410; however, as instrument 500 is inserted within lumen 402 of sterile shield 400, the corresponding actuator 520 will contact moveable slider 410 and push moveable slider 410 translationally along pathway 412 such that the other side of moveable slider 410 contacts the corresponding receptacle 310, thereby ensuring proper and automatic alignment of actuator 520, moveable slider 410, and receptacle 310.

In one embodiment, receptacle 310, moveable slider 410, and actuator 520 may be arranged such that they collectively allow for reverse insertion of instrument 500 within sterile shield 400. For example, instrument 500 may first be inserted within a trocar, then pulled back to insert sterile shield 400 in a distal-to-proximal direction, e.g., from lower component 406 toward upper component 404.

Teleoperated surgical instrument 10 may have a control system in communication with one or more sensors disposed on teleoperated surgical instrument 10 and an alarm system. For example, if an actuation of handle 100 causes receptacle 310 to be in a position that when instrument 500 is inserted within sterile shield 400, actuator 520 attempts to cause an undesirable articulation of end-effector 506, e.g., due to inherent design of the instrument or potential collision with a trocar when the end-effector is still inside the trocar lumen upon instrument insertion, at least one of the one or more sensors may detect lack of proper alignment, e.g., a torque sensor integrates within drive unit 304 or by measuring the current of motor 306, and the control system may generate an alarm via the alarm system based on the detection by the sensor. The control system may alternatively, cause drive unit 304 to move receptacle 310 in a direction that improves alignment.

As shown in FIG. 7C, when instrument 500 is positioned within sterile shield 400, rotatable portion 510 of instrument 500 may be rotated via grooves 516 such that locking pins 514 enters slit 408 of sterile shield 400 to secure instrument 500 within sterile shield 400.

Figure 8:
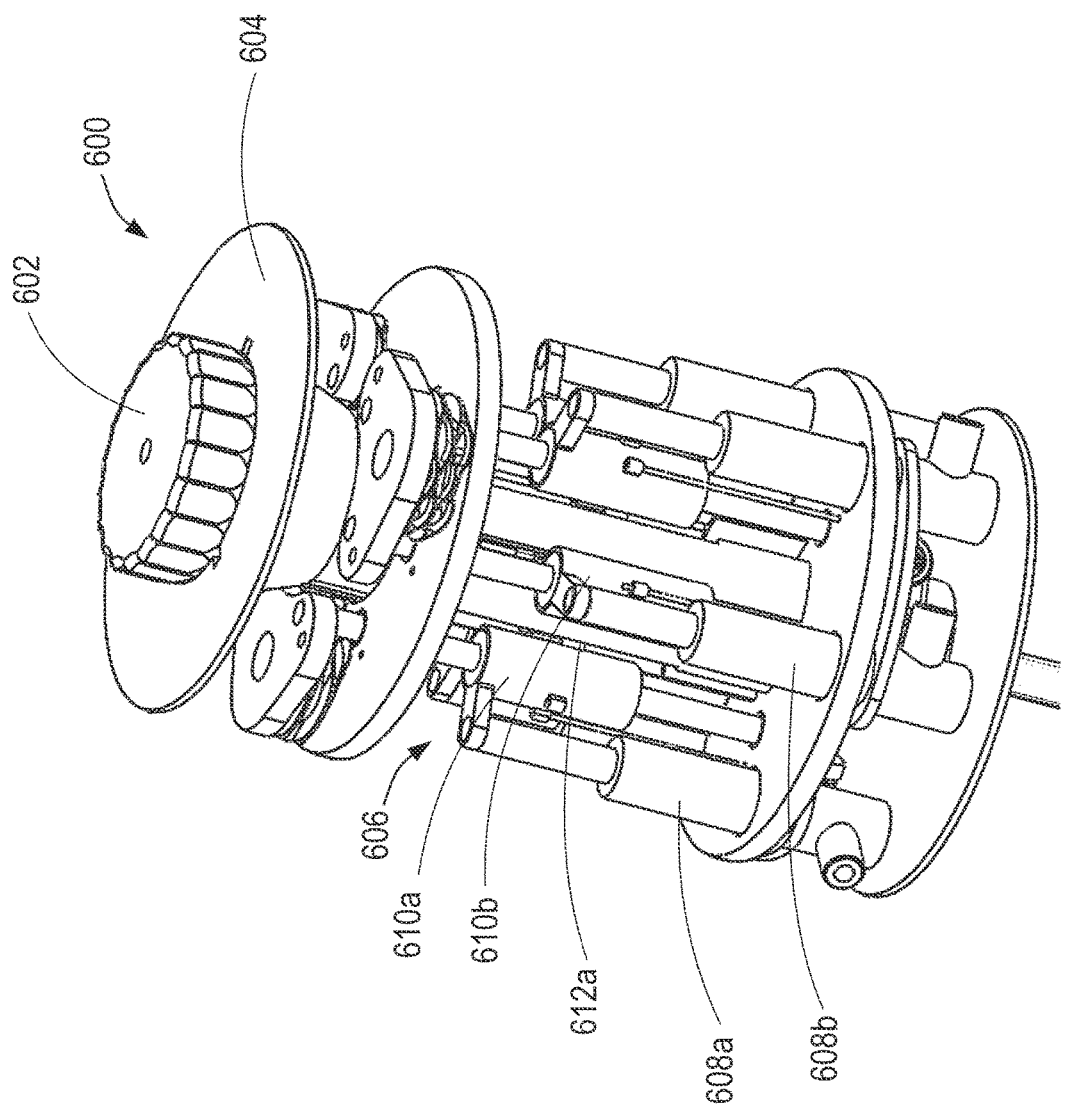
FIG. 8 shows another exemplary translational instrument interface constructed in accordance with the principles of the present invention.

Referring now to FIG. 8, another exemplary translational instrument interface constructed in accordance with another aspect is described. Translational instrument interface 600 is constructed similarly to translational instrument interface 200 of FIG. 2, such that instrument 602 corresponds with instrument 500 of translational instrument interface 200, and sterile interface 604 corresponds with sterile shield 400 of translational instrument interface 200. Translational instrument interface 600 differs from translational instrument interface 200 in that drive unit 606 has a pair of single-acting hydraulic cylinders 608a and 608b instead of electrical motor 304. Hydraulic cylinders 608a and 608b are actuated responsive to mechanical movement at the handle of the teleoperated surgical instrument. Each of hydraulic cylinders 608a and 608b is directly coupled to first and second linear pointers 610a and 610b, respectively, wherein each of first and second linear pointers 610a and 610b is coupled to first and second receptacles 612a and 612b (not shown), which are coupled to the end-effector of instrument 602 in the same manner as translational instrument interface 200, such that hydraulic cylinders 608a and 608b may actuate movement of the end-effector of instrument 602. As such, translational instrument interface 200 may be coupled to a slave unit of a purely mechanical teleoperated surgical robot, wherein the handle does not include any electronic instruments such that the end-effector of instrument 602 is actuated by force transmission elements extending from the end-effector, through the master-slave configuration of the surgical robot, to the handle. In another embodiment, the drive unit includes a pneumatic drive element instead of hydraulic cylinders.

Figure 9A:
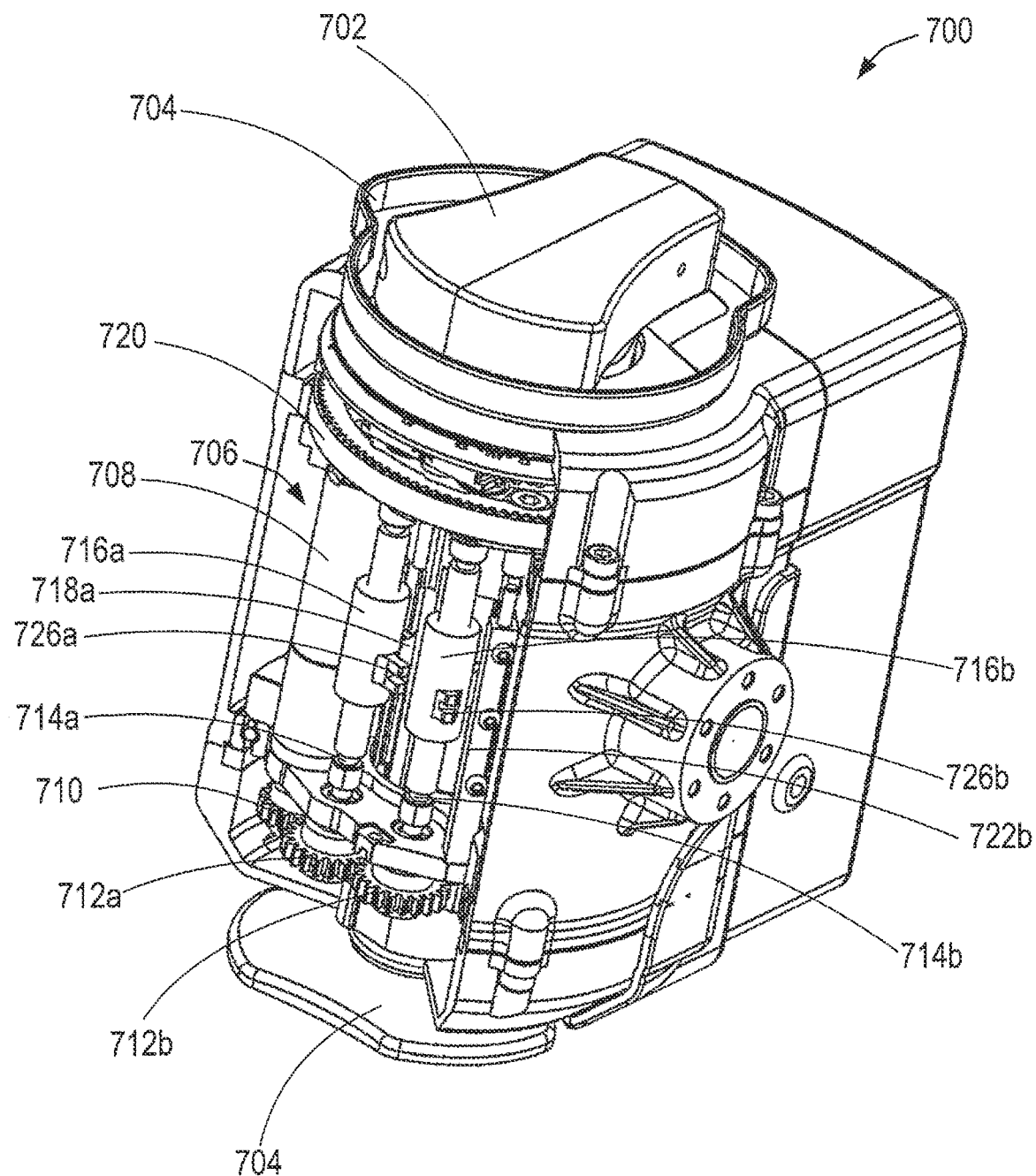
FIGS. 9A-9D show yet another exemplary translational instrument interface constructed in accordance with the principles of the present invention.
Figure 9B:
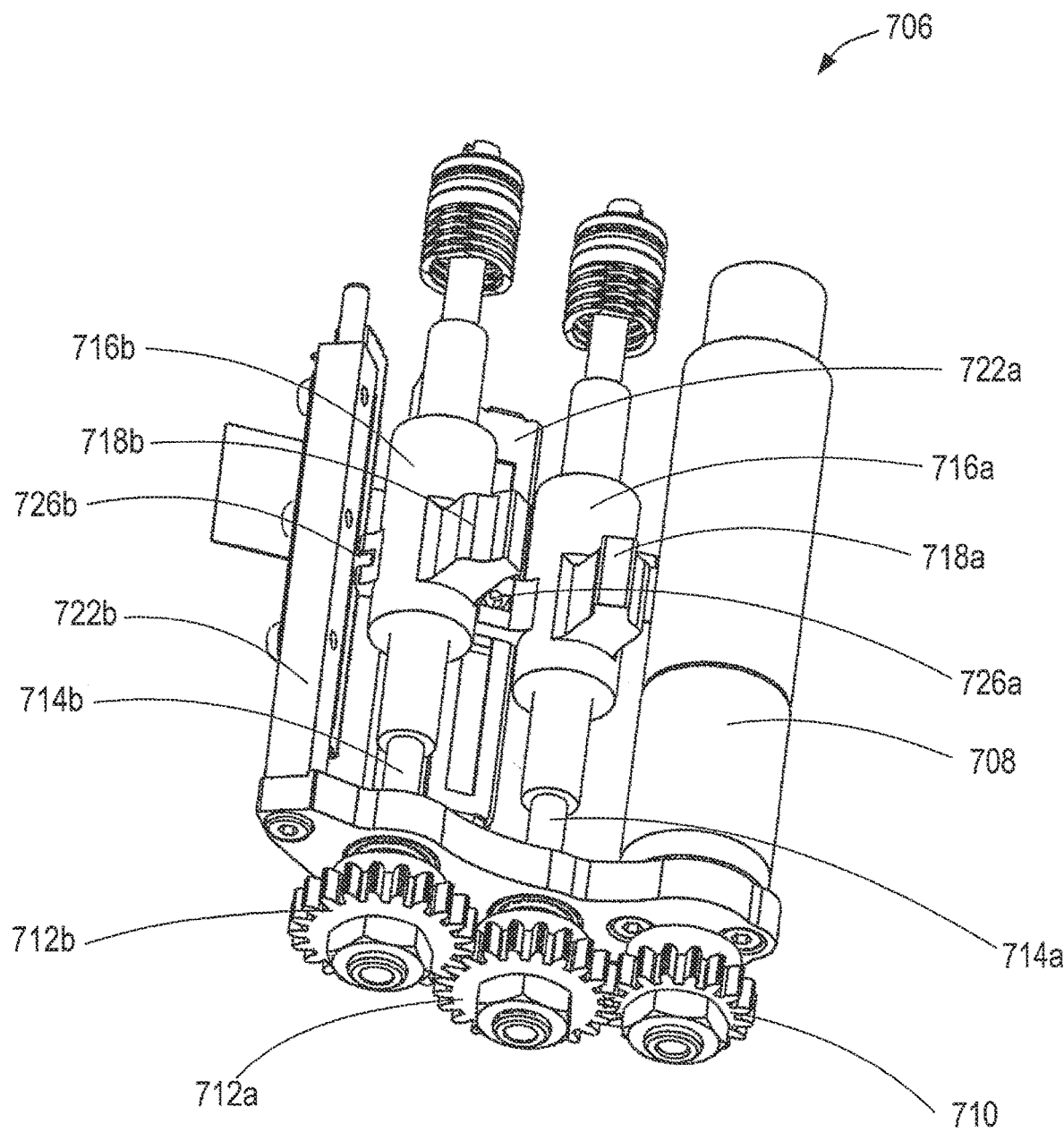

Referring now to FIG. 9A, yet another exemplary translational instrument interface constructed in accordance with another aspect is described. Translational instrument interface 700 is constructed similarly to translational instrument interface 200 of FIG. 2, such that instrument 702 corresponds with instrument 500 of translational instrument interface 200, and sterile interface 704 corresponds with sterile shield 400 of translational instrument interface 200. Translational instrument interface 700 differs from translational instrument interface 200 in that drive unit 706 transmits linear motion to instrument 702 via a system of lead screws and gears instead of cables and pulleys. For example, as illustrated in FIGS. 9A and 9B, drive unit 706 includes motor 708 coupled to motor gear 710. Motor gear 710 is operatively engaged with first and second actuator gears 712a and 712b. As shown, motor gear 710 and first and second actuator gears 712a and 712b are operatively engaged such that rotation of motor gear 710 in, for example, a clockwise direction, will cause adjacent first actuator gear 712a to rotate in the opposite direction, e.g., counter-clockwise, which will then cause second actuator gear 712b to rotate in a direction opposite to that of first actuator gear 712a, e.g., clockwise. Accordingly, first and second actuator gears 712a and 712b will move in opposite directions.

Each of first and second actuator gears 712a and 712b is coupled to first and second leadscrews 714a and 714b, respectively, which in turn are each operatively engaged with first and second leadscrew nuts 716a and 716b, respectively. For example, when motor 708 causes first leadscrew 714a to rotate via motor gear 710 and first actuator gear 712a, first leadscrew nut 716 will translationally move up or down, depending on the rotational direction of first leadscrew 714a, along the longitudinal axis of first leadscrew 714a. As illustrated in FIG. 9B, each drive unit 706 may include first and second linear sensors 722a and 722b, for sensing the linear position of first and second leadscrew nuts 716a and 716b, respectively. For example, each of first and second leadscrew nuts 716a and 716b may include first and second sensor tags 726a and 726b coupled thereon, respectively, such that first and second linear sensors 722a and 722b senses the linear position of first and second leadscrew nuts 716a and 716b based on the sensed position of first and second sensor tags 726a and 726b. In addition, first and second linear sensors 722a and 722b may be in electrical communication with the control system of teleoperated surgical instrument 10 to transmit information indicative of the position of the end-effector components.

Figure 9C:
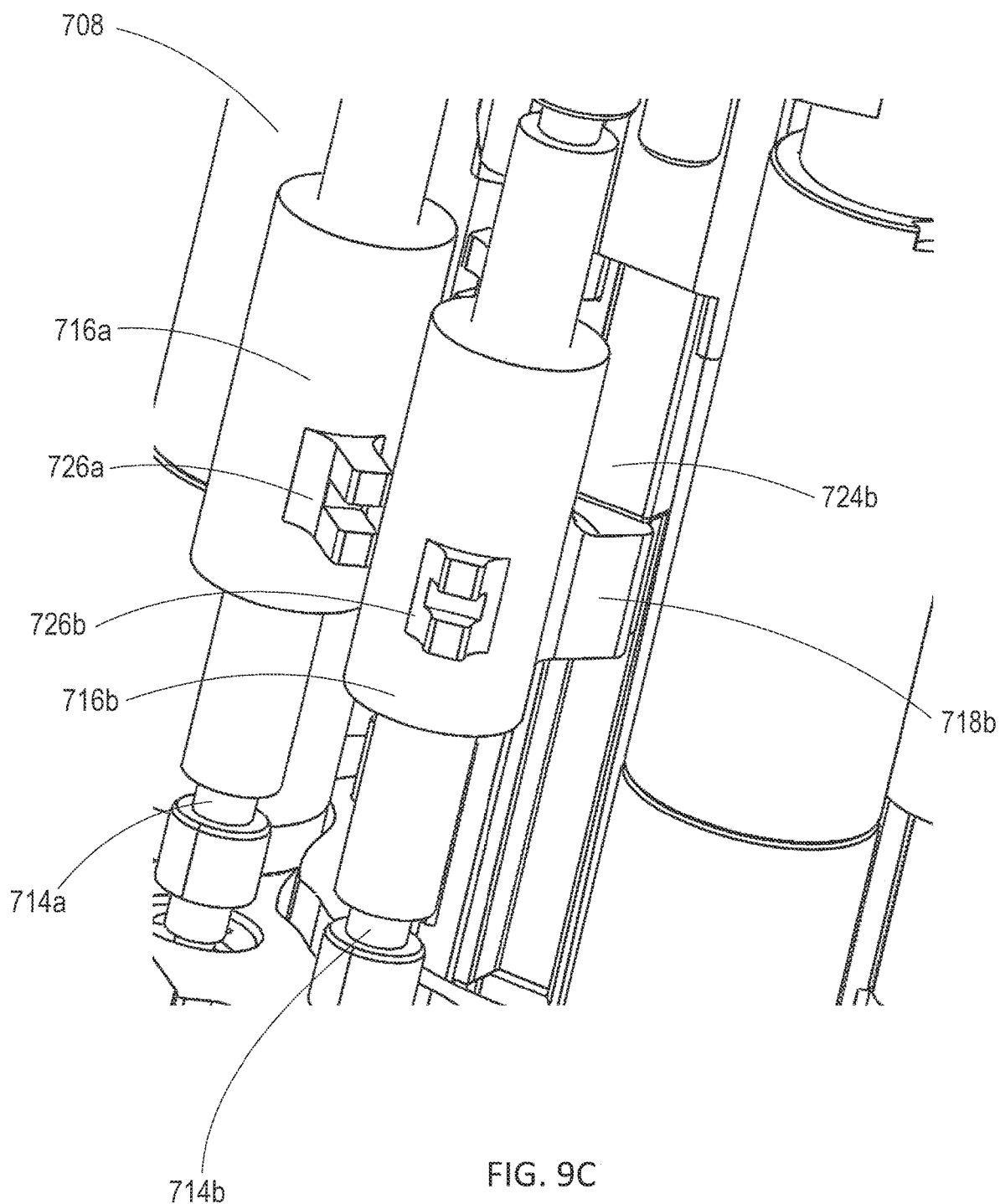
Figure 9D:
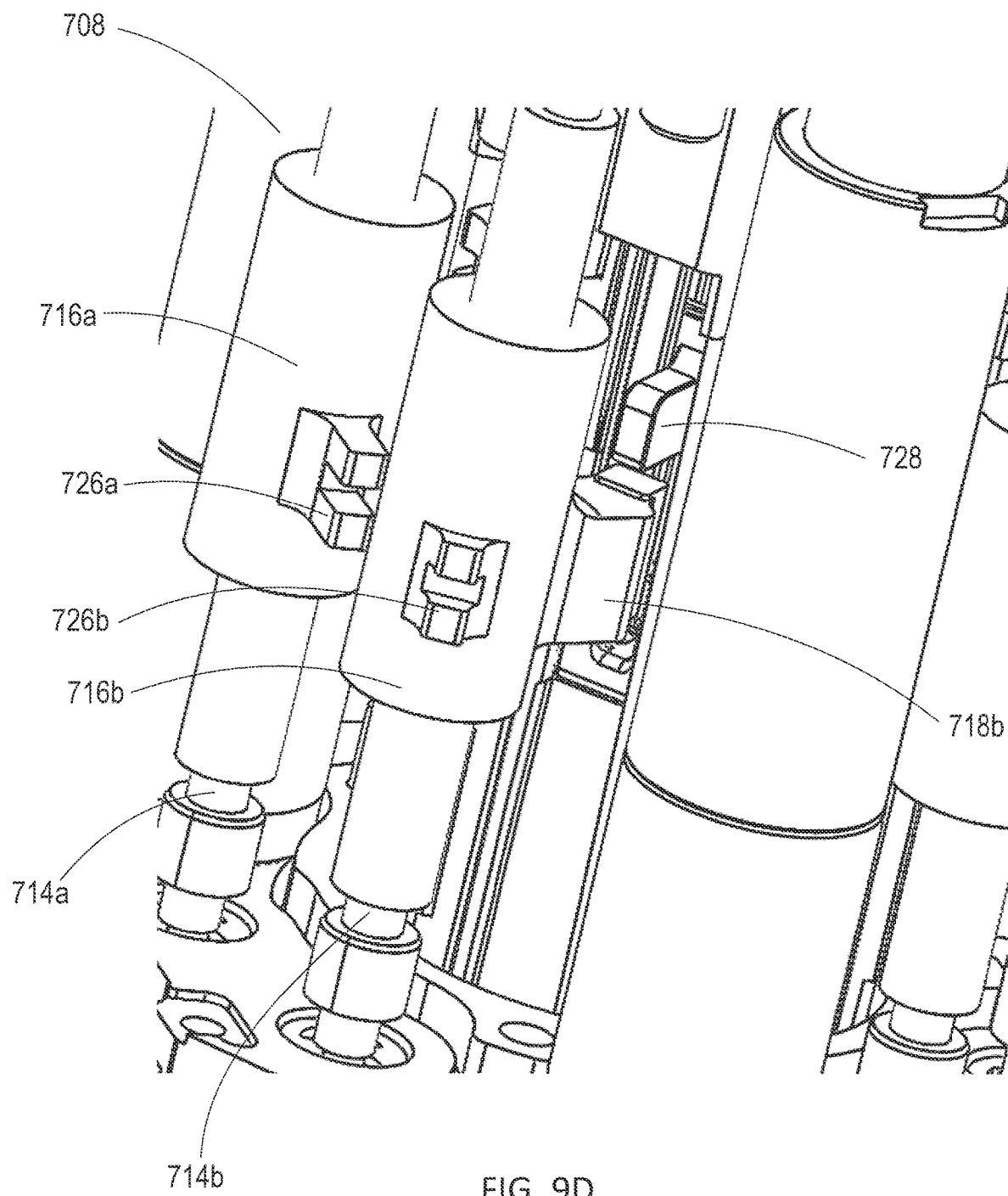

Referring back to FIG. 9A, each of first and second leadscrew nuts 716a and 716b is coupled to first and second receptacles 718a and 718b, respectively, which are each coupled to the actuators of instrument 702 as described above. Thus, as first and second actuator gears 712a and 712b move in opposite directions, receptacles 718a and 718b will move translationally in opposite directions, e.g., as leadscrew nut 716a moves upward, leadscrew nut 716b will move downward, and vice versa. In addition, first and second receptacles 718a and 718b prevent rotation of first and second leadscrew nuts 716a and 716b about the longitudinal axes of first and second leadscrews 714a and 714b, such that only translational movement along the longitudinal axes of first and second leadscrews 714a and 714b is permitted. For example, first and second receptacles 718a and 718b are coupled to the actuators of instrument 702 via first and second sterile interface sliders 724a (not shown) and 724b, respectively, as illustrated in FIG. 9C, which engage with first and second receptacles 718a and 718b so as to prevent rotation thereof. FIG. 9D illustrates second receptacle 718b coupled to actuator 728 of instrument 702 with second sterile interface slider 724b omitted for clarity.

As will be understood by a person having ordinary skill in the art, translational instrument interface 700 may include more than one drive unit, each drive unit designed to transmit translational motion to instrument 702, to thereby actuate the end-effector of instrument 702 in a corresponding degree of freedom as described above. For example, translational instrument interface 700 may include three drive units such that micro movements at the end-effector in three degrees-of-freedom, e.g., open/close, pitch, and yaw, are actuated electromechanically. The seventh degree-of-freedom, pronosupination, may be controlled electromechanically or mechanically via pronosupination pulley 720. For example, pronosupination pulley 720 may be actuated via a system of cables and pulley or a plurality of rigid links, or via a fourth motor coupled to translational instrument interface 700 via, e.g., a cable.

Figure 10A:
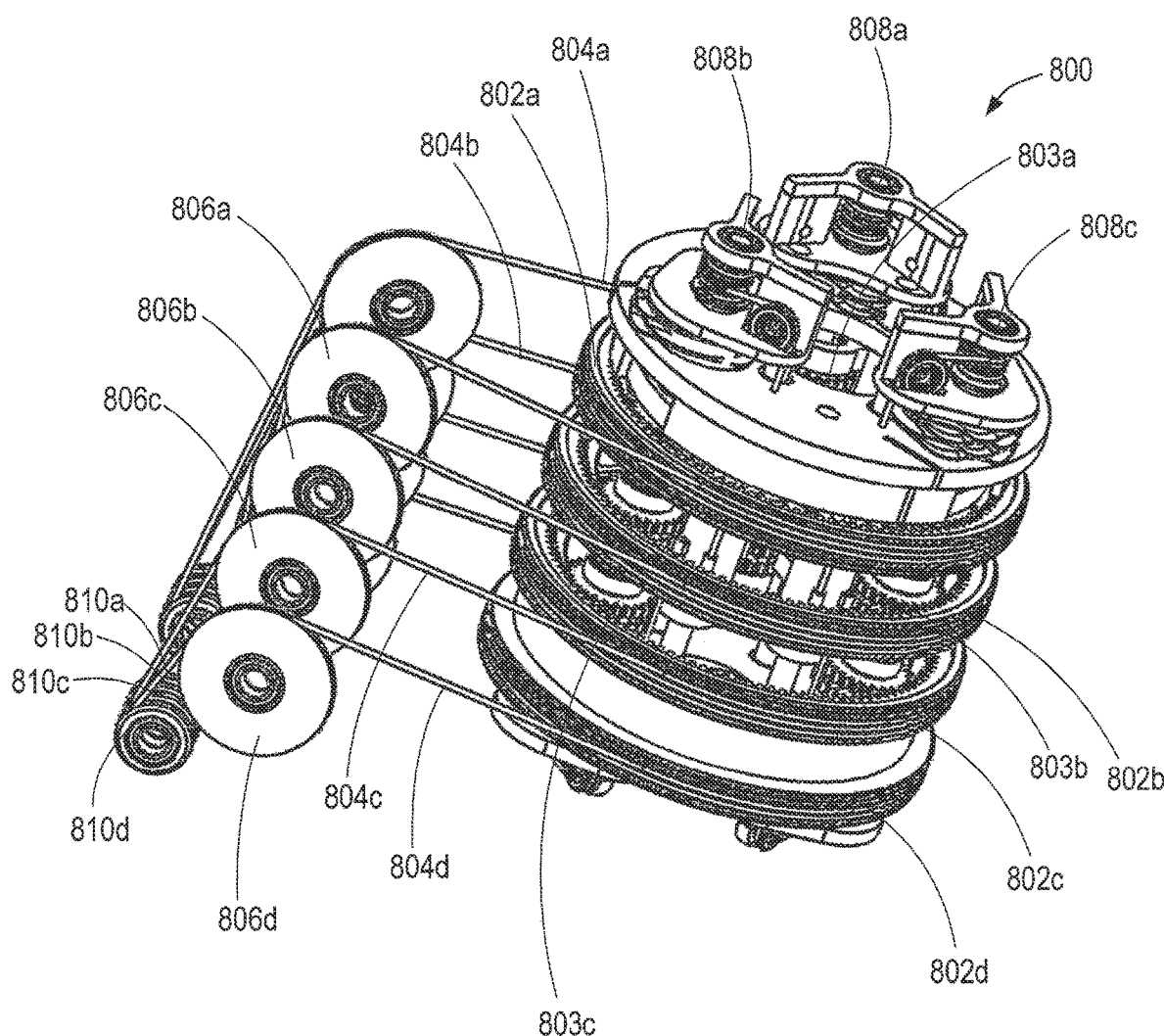
FIGS. 10A and 10B show another exemplary slave hub wherein seven degrees-of-freedom are actuated mechanically.

Referring now to FIG. 10A, an exemplary slave hub wherein seven degrees-of-freedom are actuated mechanically is described. Slave hub 800 is constructed similarly to slave hub 300 of FIG. 3. For example, driver pulleys 808a, 808b, and 808c correspond with driver pulleys 312. Slave hub 800 differs from slave hub 300 in that instead of one or more motors causing the driver pulleys of slave hub 800 to rotate, each of driver pulleys 808a, 808b, and 808c is coupled to planetary gears 803a, 803b, and 803c, respectively, each dedicated to actuate the end-effector of an instrument coupled to slave hub 800 in a respective degree-of-freedom, e.g., open/close, yaw, and pitch. Thus, actuation of planetary gears 803a, 803b, and 803c causes driver pulleys 808a, 808b, and 808c to rotate, thereby transmitting linear motion to the linear pointers of slave hub 800 to actuate one of three degrees-of-freedom of the end-effector. Each of planetary gears 803a, 803b, and 803c is coupled to one of actuation pulleys 802a, 802b, or 802c suspended about slave hub 800, which in turn are each coupled to one of pair of pulleys 806a, 806b, 806c, respectively, via 804a, 804b, 804c. The corresponding pulleys of each pair of pulleys of pair of pulleys 806a, 806b, 806c rotate in an equal amount in an opposite direction to each other to thereby rotate the respective actuation pulley and driver pulley. In addition, slave hub 800 includes pronosupination pulley 802*d* for actuating the seventh rotational degree-of-freedom, pronosupination. For example, pronosupination pulley 802*d* may be fixed to slave hub 800 such that rotation thereof via cable 804*d* and pair of pulleys 806*d* causes slave hub 800 to rotate, thereby causing the teleoperated surgical instrument and thus the end-effector to rotate.

Figure 10B:
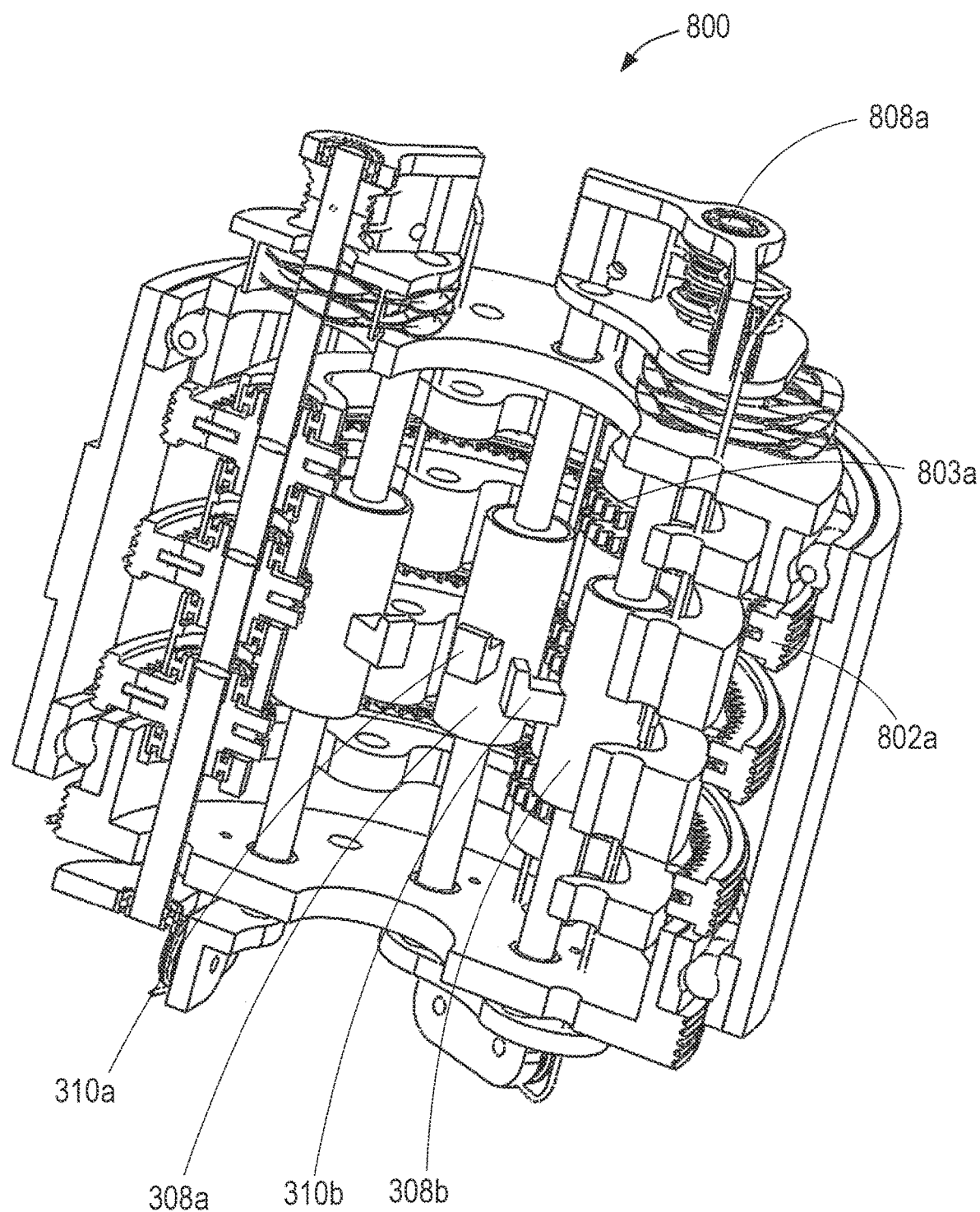

As illustrated in FIG. 10B, rotation of actuation pulley 802*a* causes rotation of planetary gear 803*a*, which causes rotation of driver pulley 808*a*. Rotation of driver pulley 808*a* causes linear pointers 308*a* and 308*b* to move translationally up or down in equal amounts in opposite directions as described above, thereby moving receptacles 310*a* and 310*b* translationally to transmit movement to the teleoperated surgical instrument to actuate the end-effector in a first degree-of-freedom.

Figure 10C:
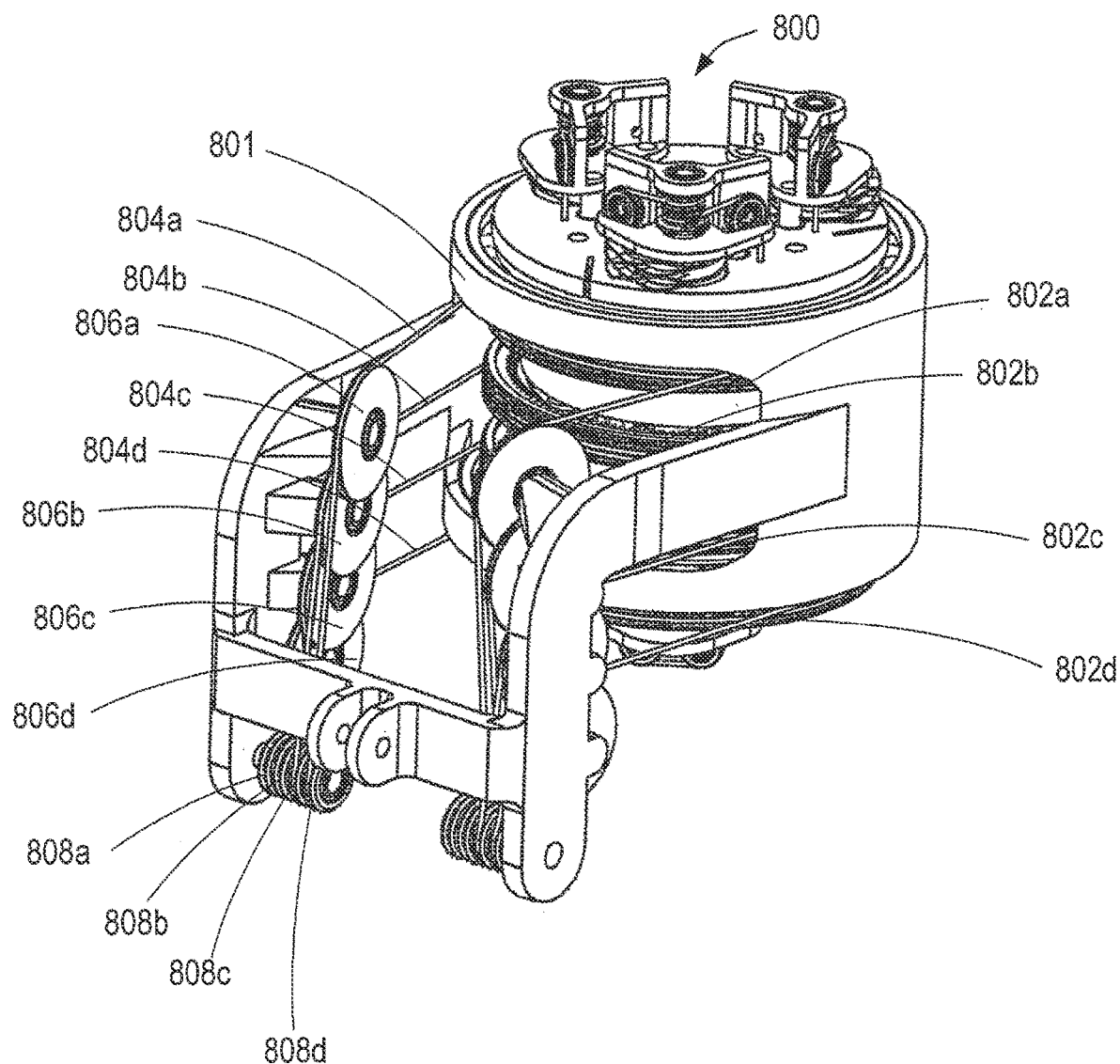
FIG. 10C illustrates an attachment interface for attaching the slave hub of FIGS. 10A and 10B to a teleoperated surgical instrument.

Referring back to FIG. 10A, each of actuation pulleys 802*a*, 802*b*, and 802*c*, and pronosupination pulley 802*d* is operatively coupled to a pair of driver pulleys 810*a*, 810*b*, 810*c*, and 810*d* via a pair of pulleys 806*a*, 806*b*, 806*c*, and 806*d* and cables 804*a*, 804*b*, 804*c*, and 804*d*, respectively. The pairs of driver pulleys 810*a*, 810*b*, 810*c*, and 810*d* are operatively coupled to the teleoperated surgical instrument such that movement at the handle of the teleoperated surgical instrument is transmitted to translational instrument interface 801, and ultimately to the end-effector. For example, slave hub 800 may be attached to teleoperated surgical instrument via attachment interface 801 as shown in FIG. 10C. As will be understood by a person having ordinary skill in the art, more or less pulleys and cables may be coupled to actuation pulleys 802*a*, 802*b*, and 802*c*, and pronosupination pulley 802*d*, for actuation thereof by the teleoperated surgical instrument.

Figure 11A:
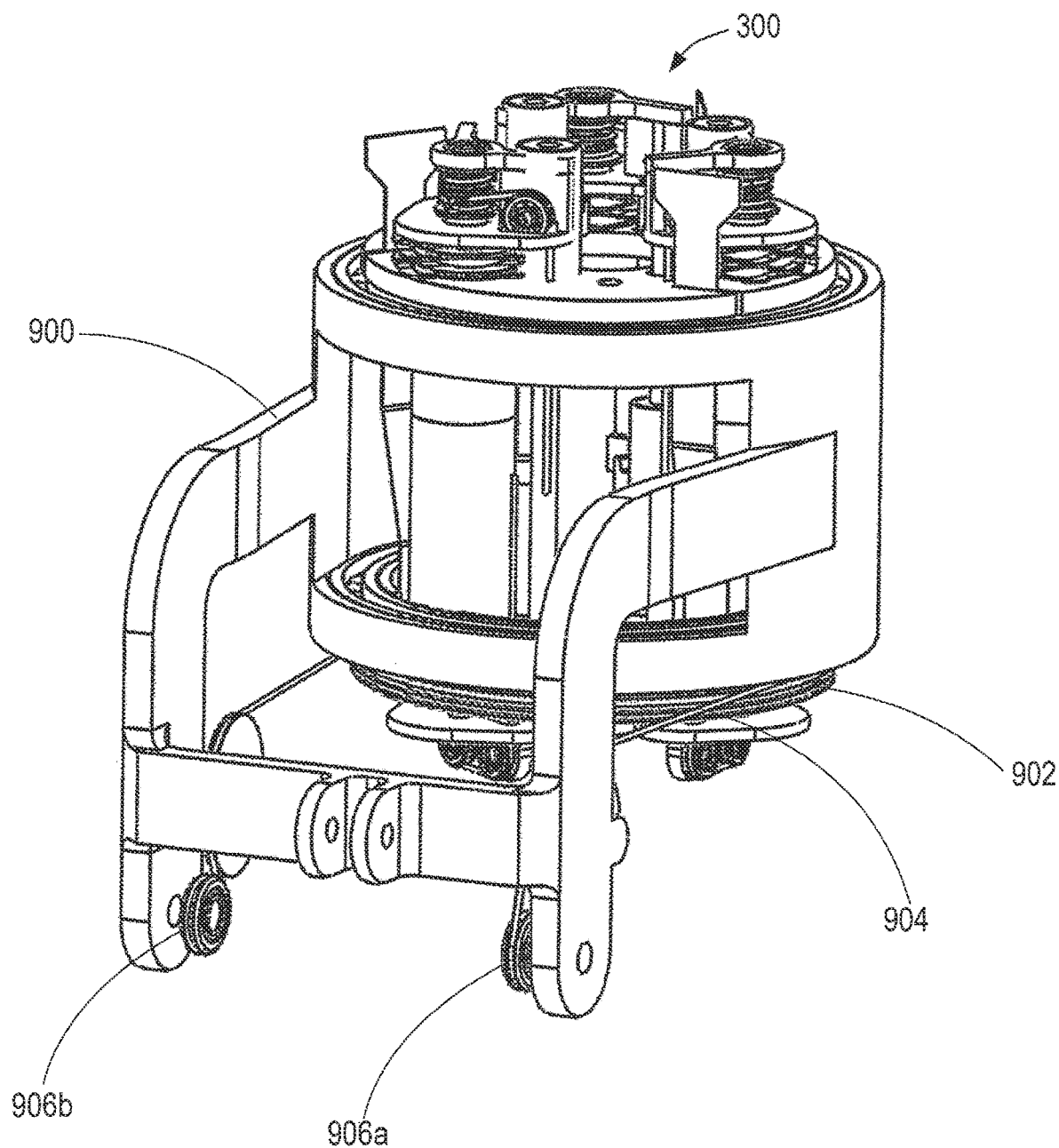
FIG. 11A illustrates an attachment interface for attaching a slave hub to a teleoperated surgical instrument having four degrees-of-freedom actuated mechanically and three degrees-of-freedom actuated electromechanically.

As described above, in various examples, a teleoperated surgical instrument with a translational instrument interface may have (i) four degrees-of-freedom actuated mechanically and three degrees-of-freedom actuated electromechanically, (ii) three degrees-of-freedom actuated mechanically and four degrees-of-freedom actuated electromechanically, or (iii) seven degrees-of-freedom actuated mechanically. Referring now to FIG. 11A, attachment interface 900 for attaching, for example, slave hub 300, to a teleoperated surgical instrument having four degrees-of-freedom actuated mechanically and three degrees-of-freedom actuated electromechanically is described. Attachment interface 900 is coupled to a distal end of the teleoperated surgical instrument, and is sized and shaped to receive slave hub 300. As shown in FIG. 11A, slave hub 300 includes pronosupination pulley 902 for moving slave hub 300 in the rotational degree-of-freedom. Pronosupination pulley 902 is operatively coupled to first and second actuation pulleys 906*a* and 906*b* via pronosupination cable 904. As first and second actuation pulleys 906*a* and 906*b* rotate in equal amounts in opposite directions, pronosupination cable 904 causes pronosupination pulley 902 to rotate slave hub 300. As will be understood by a person having ordinary skill in the art, any slave hub or translational instrument interface described herein may be coupled to attachment interface 900, e.g., translational instrument interface 600 or translational instrument interface 700.

Figure 11B:
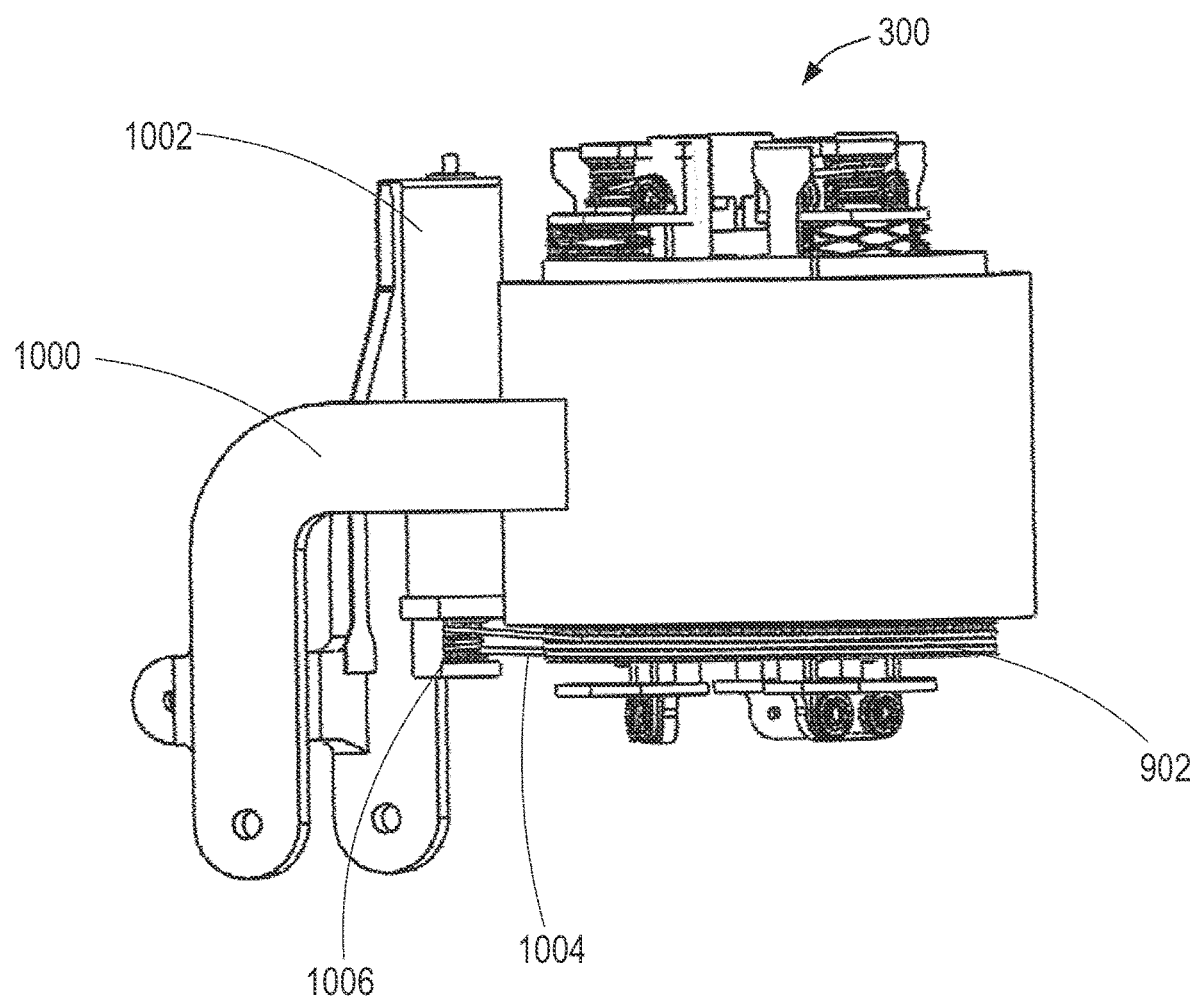
FIG. 11B illustrates an attachment interface for attaching a slave hub to a teleoperated surgical instrument having three degrees-of-freedom actuated mechanically and four degrees-of-freedom actuated electromechanically.

Referring now to FIG. 11B, attachment interface 1000 for attaching, for example, slave hub 300, to a teleoperated surgical instrument having three degrees-of-freedom actuated mechanically and four degrees-of-freedom actuated electromechanically is described. Attachment interface 1000 is similar to attachment interface 900 except that instead of first and second actuation pulleys 906*a* and 906*b* for actuating pronosupination pulley 902, attachment interface 1000 includes motor 1002 and actuation pulley 1006. For example, motor 1002 causes pronosupination pulley 902 to rotate by rotating actuation pulley 1006 which is operatively coupled to pronosupination pulley 902 via pronosupination cable 1004. As will be understood by a person having ordinary skill in the art, any slave hub or translational instrument interface described herein may be coupled to attachment interface 1000, e.g., translational instrument interface 600 or translational instrument interface 700.

Figure 12:
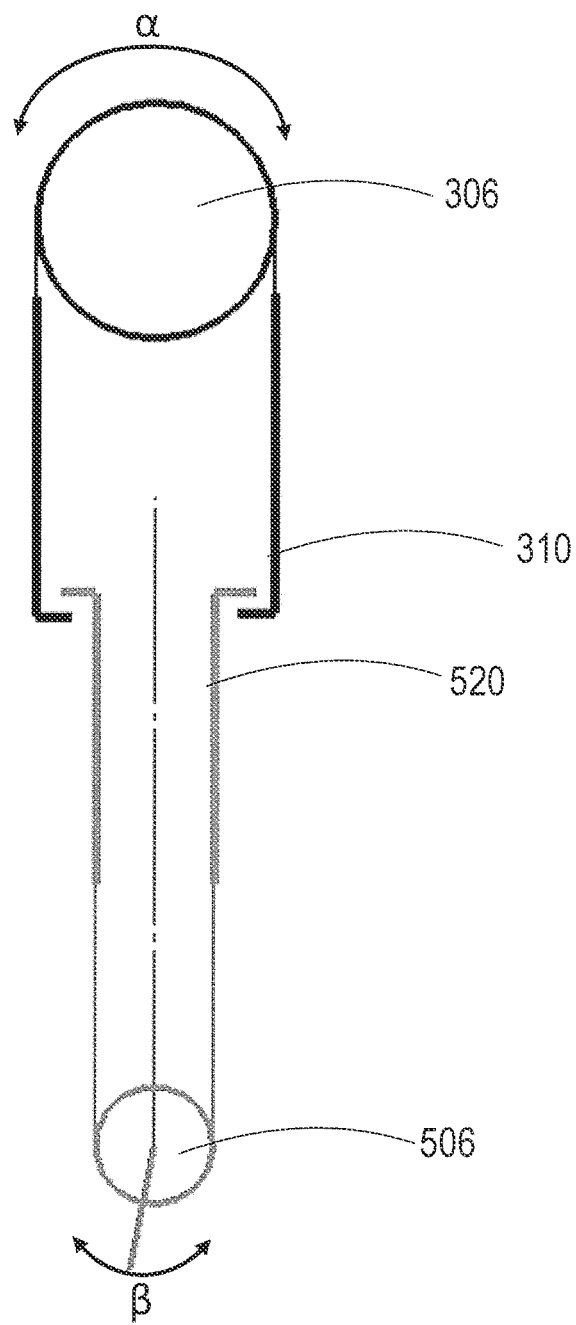
FIG. 12 depicts the translation movement of the translational instrument interface in accordance with an exemplary embodiment.

As shown in FIG. 12, a movement α of receptacle 310 caused by motor 306 will efficiently be translationally transmitted to actuator 520, thereby causing corresponding movement β at end-effector 506.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for actuating an instrument of a surgical robot, the method comprising:
    coupling a sterile barrier to a slave hub of the surgical robot by inserting a first component of the sterile barrier into a proximal end of a lumen extending through the slave hub and a second component of the sterile barrier into a distal end of the lumen;
    coupling an instrument to the slave hub of the surgical robot via the sterile barrier such that a pair of engagers of an actuator disposed in a proximal region of the instrument releasably couples to a respective extension of a pair of receptacles of the slave hub, the actuator coupled to an end-effector disposed in a distal region of the instrument; and
    actuating a drive unit coupled to the pair of receptacles to induce translational movement at a first engager of the pair of engagers in a first direction and to induce translational movement at a second engager of the pair of engagers in an opposite direction to thereby move the end-effector in a degree-of-freedom for performing surgery.

2. The method of claim 1, wherein coupling the instrument to the slave hub of the surgical robot comprises rotating a rotatable portion of an instrument head of the instrument such that a locking pin coupled to the rotatable portion engages with a slit of the sterile barrier coupled to the slave hub.

3. The method of claim 1, wherein coupling the instrument to the slave hub of the surgical robot comprises axially aligning a key of an instrument head of the instrument with the sterile barrier coupled to the slave hub.

4. The method of claim 1, wherein actuating the drive unit induces translational movement at the first and second engagers parallel to a longitudinal axis of the instrument along a pathway at the proximal region of the instrument.

5. The method of claim 1, wherein actuating the drive unit to induce translational movement at the first and second engagers comprises actuating rotary movement of the drive unit to induce translational movement at the first and second engagers via a system of cables and pulleys.

6. The method of claim 1, wherein actuating the drive unit to induce translational movement at the first and second engagers comprises actuating rotary movement of the drive unit to induce translational movement at the first and second engagers via a system of gears, leadscrews, and leadscrew nuts.

7. The method of claim 1, wherein coupling the instrument to the slave hub of the surgical robot comprises releasably coupling a second pair of engagers of the actuator to a respective extension of a second pair of receptacles of the slave hub, the method further comprising:
actuating a second drive unit coupled to the second pair of receptacles to induce translational movement at a first engager of the second pair of engagers in the first direction and to induce translational movement at a second engager of the second pair of engagers in the opposite direction to thereby move the end-effector in a second degree-of-freedom.

8. The method of claim 7, wherein coupling the instrument to the slave hub of the surgical robot comprises releasably coupling a third pair of engagers of the actuator to a respective extension of a third pair of receptacles of the slave hub, the method further comprising:
actuating a third drive unit coupled to the third pair of receptacles to induce translational movement at a first engager of the third pair of engagers in the first direction and to induce translational movement at a second engager of the third pair of hook shaped engagers in the opposite direction to thereby move the end-effector in a third degree-of-freedom.

9. The method of claim 1, further comprising disposing of the instrument after a single use.

10. The method of claim 1, wherein the actuator is coupled to the end-effector disposed in the distal region of the instrument via a plurality of force transmitting elements, the method further comprising tensioning the plurality of force transmitting elements via at least one tension cable coupled to the actuator.

11. The method of claim 1, further comprising tensioning the pair of receptacles via at least one tension cable of the slave hub coupled to the pair of receptacles.

12. The method of claim 1, further comprising rotating the slave hub about an axis to rotate the end-effector about the axis.

13. The method of claim 1, further comprising detecting information about the instrument via an identification tag of the instrument.

14. The method of claim 13, further comprising encoding the identification tag with at least one of: an instrument type, serial number, calibration data, range-of-motion data, end-effector kinematics, or controlling offsets.

15. The method of claim 1, wherein the slave hub is coupled to a slave unit comprising a plurality of slave links and slave joints, the slave unit operatively coupled to a master unit comprising a handle and a plurality of master links and master joints, the method further comprising:
reproducing movement of the master unit at the slave unit; and
reproducing movement of the handle by the end-effector.

16. The method of claim 1, wherein coupling the sterile barrier to the slave hub comprises:
engaging the first component of the sterile barrier with the second component when the first component and the second component of the sterile barrier have been inserted into the lumen.

17. The method of claim 16, wherein coupling the sterile barrier to the slave hub further comprises orientating at least one of the first component or the second component relative to the lumen extending through the slave hub via an asymmetric shape of the at least one of the first component or the second component.

18. The method of claim 1, wherein coupling the instrument to the slave hub comprises coupling the pair of engagers to a pair of slide elements of the sterile barrier, such that the pair of slide elements are coupled between the pair of engagers and the pair of receptacles.

19. The method of claim 18, wherein the pair of slide elements automatically align the pair of receptacles with the actuator.

* * * * *